US006821726B1

(12) United States Patent
Dahm et al.

(10) Patent No.: US 6,821,726 B1
(45) Date of Patent: Nov. 23, 2004

(54) METHOD FOR QUANTITATIVELY ANALYZING TUMOR CELLS IN A BODY FLUID AND TEST KITS SUITED THEREFOR

(76) Inventors: Michael W. Dahm, Gleimstrasse 2, D-81677 München (DE); Robert C. Phelps, Dohlenweg 6, 85757 Karlsfeld (DE); Carsten Brockmeyer, Fellerer Strasse 2, D-85354 Freising (DE)

( * ) Notice: Subject to any disclaimer, the term of this patent is extended or adjusted under 35 U.S.C. 154(b) by 0 days.

(21) Appl. No.: 09/601,645
(22) PCT Filed: Feb. 3, 1999
(86) PCT No.: PCT/EP99/00716
§ 371 (c)(1), (2), (4) Date: Aug. 4, 2000
(87) PCT Pub. No.: WO99/40221
PCT Pub. Date: Aug. 12, 1999

(30) Foreign Application Priority Data

Feb. 4, 1998 (DE) ......................................... 198 04 372

(51) Int. Cl.[7] ........................... C07H 21/04; C12Q 1/68
(52) U.S. Cl. ....................... 435/6; 435/91.1; 435/91.2; 536/23.1; 536/24.3
(58) Field of Search ........................ 435/6, 91.1, 91.2; 536/23.1, 24.3

(56) References Cited

U.S. PATENT DOCUMENTS

| | | | |
|---|---|---|---|
| 3,741,400 A | 6/1973 | Dick | 210/516 |
| 3,887,464 A | 6/1975 | Ayres | 210/117 |
| 3,945,928 A | 3/1976 | Ayres | 210/516 |
| 4,683,195 A | 7/1987 | Mullis et al. | 435/6 |
| 4,683,202 A | 7/1987 | Mullis | 435/91 |
| 4,889,818 A | 12/1989 | Gelfand et al. | 435/194 |
| 4,965,188 A | 10/1990 | Mullis et al. | 435/6 |
| 5,270,171 A | 12/1993 | Cercek et al. | 435/29 |
| 5,298,165 A * | 3/1994 | Oka et al. | 210/645 |
| 5,487,973 A | 1/1996 | Nilsen et al. | 435/6 |
| 5,577,513 A | 11/1996 | Van Vlasselaer | 128/765 |
| 5,583,016 A | 12/1996 | Villeponteau et al. | 435/91.3 |
| 5,648,223 A * | 7/1997 | Van Vlassalaer | 435/7.23 |
| 5,663,051 A | 9/1997 | Vlasselaer | 435/7.23 |
| 5,726,019 A * | 3/1998 | Sidransky | 435/6 |
| 5,770,422 A | 6/1998 | Collins | 435/194 |
| 5,776,679 A | 7/1998 | Villeponteau et al. | 435/6 |
| 5,807,744 A | 9/1998 | Berneman et al. | 435/372 |
| 5,840,502 A | 11/1998 | Van Vlasselaer | 435/7.21 |
| 5,856,096 A | 1/1999 | Windle et al. | 435/6 |
| 6,025,156 A * | 2/2000 | Gwynn et al. | 435/69.1 |
| 6,166,178 A * | 12/2000 | Cech et al. | 530/324 |
| 6,177,080 B1 | 1/2001 | Fleckenstein et al. | 424/186.1 |

FOREIGN PATENT DOCUMENTS

| | | |
|---|---|---|
| EP | 0566252 | 3/1993 |
| EP | 0875202 | 11/1998 |
| EP | 0566252 | 1/1999 |
| GB | 2260811 | 4/1993 |
| GB | 2 260 811 * | 4/1993 |
| GB | 2317891 | 4/1998 |
| WO | 9007641 | 7/1990 |
| WO | 9601835 | 1/1996 |
| WO | 9607097 | 3/1996 |
| WO | WO 9712246 * | 4/1997 |
| WO | 9718322 | 5/1997 |
| WO | 9721488 | 6/1997 |
| WO | 9802581 | 1/1998 |
| WO | 9837181 | 2/1998 |
| WO | 9814592 | 4/1998 |
| WO | 9822825 | 5/1998 |
| WO | 9859040 | 12/1998 |
| WO | 0046585 | 8/2000 |

OTHER PUBLICATIONS

Gelmini et al. "Quantitative polymerase chain reaction–based homogeneous assay with fluorogenic probes to measure c–erbB–2 oncogene amplificiation". Clinical Chemistry. vol. 43, No. 5, pp. 752–758, 1997.*
Nakamura et al. Science 277:955–959 (Aug. 15, 1997).*
Altschul et al., Basic Local Alignment Search Tool, *J. Mol. Biol.* 215:403–10 (1990).
BCSH Blood Transfusion Task Force: Voak, D. et al., Guidelines for the Collection, processing and storage of human bone marrow and peripheral stem cells for transplantation, *Transfusion Medicine* 4:165–72 (1994).
Blasco et al., Differential regulation of telomerase activity and telomerase RNA during multi–stage tumorigenesis, *Nature Genetics* 12(2):200–4 (1996).
Boom et al., Rapid and Simple Method for Purification of Nucleic Acids, *J. Clinical Microbiology* 28(3):495–503 (1990),
Hexal Gentech product literature for OncoQuick® centrifugation tube available at http://www.hexal–gentech.com/products/; website last update may 2001.
Asai et al., "Telomere legnth, telomere activity and telomerase RNA expression in human esophageal cancer cells:Correlation with cell proliferation, differentiation and chemosensitivity to anticancer drugs" *Anticancer Research* 18:1465–1472 (1998).
Blasco et al., "Functional characterization and developmental regulation of mouse telomerase RNA" *Science* 269:1267–70 (1995).

(List continued on next page.)

Primary Examiner—Jeffrey Fredman
Assistant Examiner—Jeanine Goldberg
(74) Attorney, Agent, or Firm—Fish & Richardson P.C.; Stephanie L. Seidman

(57) ABSTRACT

The invention relates to a method for quantitatively analyzing tumor cells in a body fluid. According to the inventive method, the test sample to be examined is first subjected to a method for accumulating or depleting tumor cells, and a reaction is carried out on the accumulated or depleted tumor cells. During the reaction, the mRNA which codes for the catalytic subunit of the telomerase is specifically amplified, and afterwards, the quantity of amplified nucleic acid is quantitatively analyzed. The invention also relates to test kits suited for the invented method.

50 Claims, 12 Drawing Sheets

OTHER PUBLICATIONS

Blasco et al., "Telomere shortening and tumor formation by mouse cells lacking telomerse RNA" *Cell* 91:25–34 (1997).

Borgen et al., Standardization of the immunocytochemical detection of cancer cells in BM and blood: 1. establishment of objective criteria for the evaluation of immunostained cells, *Cytotherapy* 1:377 (1999).

Kim et al., "Advanced in quanfification and characterization of telomerase activity by the telomeric repeat amplification protocol (TRAP)" *Nuc. Acids Res.* 25(13):2595–2597.

Mehle et al., "Telomere Shortening in Renal Cell Carcinoma" *Cancer Res* 54:236–241 (1994).

Mueller et al., "Self–sustained sequence replication (3SR): an alternative to PCR" Histochemical *Cell Biology* 108:431–7 (1997).

Nilsen et al., Dendritic Nucleic Acid Structures, *J. Theor. Biol.* 187:273–284 (1997).

Sano et al., "Telomerase activity in 144 brain tumours" *Brit. J. of Cancer* 77(10):1633–1637 (1998).

van Gemen et al., "Quantification of HIV–1 RNA in plasma using NASBA during HIV–1 primary infection" *J. Virol. Meth.* 43:177–188 (1993).

Zhong et al., Sensitivity and Specificity of Immunocytochemistry for the Detection of Tumour Cells in the Bone Marrow of Patients with Breast Cancer, *Tumordiagn. u. Ther.* 20:39 (1999).

\* cited by examiner

```
   1 GCAGCGCTGC GTCCTGCTGC GCACGTGGGA AGCCCTGGCC CCGGCCACCC CCGCGATGCC
  61 GCGCGCTCCC CGCTGCCGAG CCGTGCGCTC CCTGCTGCGC AGCCACTACC GCGAGGTGCT
 121 GCCGCTGGCC ACGTTCGTGC GGCGCCTGGG GCCCCAGGGC TGGCGGCTGG TGCAGCGCGG
 181 GGACCCGGCG GCTTTCCGCG CGCTGGTGGC CCAGTGCCTG GTGTGCGTGC CCTGGGACGC
 241 ACGGCCGCCC CCCGCCGCCC CCTCCTTCCG CCAGGTGTCC TGCCTGAAGG AGCTGGTGGC
 301 CCGAGTGCTG CAGAGGCTGT GCGAGCGCGG CGCGAAGAAC GTGCTGGCCT TCGGCTTCGC
 361 GCTGCTGGAC GGGGCCCGCG GGGGCCCCCC CGAGGCCTTC ACCACCAGCG TGCGCAGCTA
 421 CCTGCCCAAC ACGGTGACCG ACGCACTGCG GGGGAGCGGG GCGTGGGGGC TGCTGCTGCG
 481 CCGCGTGGGC GACGACGTGC TGGTTCACCT GCTGGCACGC TGCGCGCTCT TTGTGCTGGT
 541 GGCTCCCAGC TGCGCCTACC AGGTGTGCGG GCCGCCGCTG TACCAGCTCG GCGCTGCCAC
 601 TCAGGCCCGG CCCCCGCCAC ACGCTAGTGG ACCCCGAAGG CGTCTGGGAT GCGAACGGGC
 661 CTGGAACCAT AGCGTCAGGG AGGCCGGGGT CCCCCTGGGC CTGCCAGCCC CGGGTGCGAG
 721 GAGGCGCGGG GGCAGTGCCA GCCGAAGTCT GCCGTTGCCC AAGAGGCCCA GGCGTGGCGC
 781 TGCCCCTGAG CCGGAGCGGA CGCCCGTTGG GCAGGGGTCC TGGGCCCACC CGGGCAGGAC
 841 GCGTGGACCG AGTGACCGTG GTTTCTGTGT GGTGTCACCT GCCAGACCCG CCGAAGAAGC
 901 CACCTCTTTG GAGGGTGCGC TCTCTGGCAC GCGCCACTCC CACCCATCCG TGGGCCGCCA
 961 GCACCACGCG GGCCCCCCAT CCACATCGCG GCCACCACGT CCCTGGGACA CGCCTTGTCC
1021 CCCGGTGTAC GCCGAGACCA AGCACTTCCT CTACTCCTCA GGCGACAAGG AGCAGCTGCG
1081 GCCCTCCTTC CTACTCAGCT CTCTGAGGCC CAGCCTGACT GGCGCTCGGA GGCTCGTGGA
1141 GACCATCTTT CTGGGTTCCA GGCCTCTGGA GCCAGGGACT CCCCGCAGGT TGCCCCGCCT
1201 GCCCCAGCGC TACTGGCAAA TGCGGCCCCT GTTTCTGGAG CTGCTTGGGA ACCACGCGCA
1261 GTGCCCCTAC GGGGTGCTCC TCAAGACGCA CTGCCCGCTG CGAGCTGCGG TCACCCCAGC
1321 AGCCGGTGTC TGTGCCCGGG AGAAGCCCCA GGGCTCTGTG GCGGCCCCCG AGGAGGAGGA
1381 CACAGACCCC CGTCGCCTGG TGCAGCTGCT CCGCCAGCAC AGCAGCCCCT GGCAGGTGTA
1441 CGGCTTCGTG CGGGCCTGCC TGCGCCGGCT GGTGCCCCCA GGCCTCTGGG CTCCAGGCA
1501 CAACGAACGC CGCTTCCTCA GGAACACCAA GAAGTTCATC TCCCTGGGGA AGCATGCCAA
1561 GCTCTCGCTG CAGGAGCTGA CGTGGAAGAT GAGCGTGCGG GACTGCGCTT GGCTGCGCAG
1621 GAGCCCAGGG GTTGGCTGTG TTCCGGCCGC AGAGCACCGT CTGCGTGAGG AGATCCTGGC
1681 CAAGTTCCTG CACTGGCTGA TGAGTGTGTA CGTCGTCGAG CTGCTCAGGT CTTTCTTTTA
1741 TGTCACGGAG ACCACGTTTC AAAAGAACAG GCTCTTTTTC TACCGGAAGA GTGTCTGGAG
1801 CAAGTTGCAA AGCATTGGAA TCAGACAGCA CTTGAAGAGG GTGCAGCTGC GGGAGCTGTC
1861 GGAAGCAGAG GTCAGGCAGC ATCGGGAAGC CAGGCCCGCC CTGCTGACGT CCAGACTCCG
1921 CTTCATCCCC AAGCCTGACG GGCTGCGGCC GATTGTGAAC ATGGACTACG TCGTGGGAGC
1981 CAGAACGTTC CGCAGAGAAA AGAGGGCCGA GCGTCTCACC TCGAGGGTGA AGGCACTGTT
2041 CAGCGTGCTC AACTACGAGC GGGCGCGGCG CCCCGGCCTC CTGGGCGCCT CTGTGCTGGG
2101 CCTGGACGAT ATCCACAGGG CCTGGCGCAC CTTCGTGCTG CGTGTGCGGG CCCAGGACCC
2161 GCCGCCTGAG CTGTACTTTG TCAAGGTGGA TGTGACGGGC GCGTACGACA CCATCCCCCA
2221 GGACAGGCTC ACGGAGGTCA TCGCCAGCAT CATCAAACCC CAGAACACGT ACTGCGTGCG
2281 TCGGTATGCC GTGGTCCAGA AGGCCGCCCA TGGGCACGTC CGCAAGGCCT TCAAGAGCCA
2341 CGTCTCTACC TTGACAGACC TCCAGCCGTA CATGCGACAG TTCGTGGCTC ACCTGCAGGA
2401 GACCAGCCCG CTGAGGGATG CCGTCGTCAT CGAGCAGAGC TCCTCCCTGA ATGAGGCCAG
2461 CAGTGGCCTC TTCGACGTCT TCCTACGCTT CATGTGCCAC CACGCCGTGC GCATCAGGGG
2521 CAAGTCCTAC GTCCAGTGCC AGGGGATCCC GCAGGGCTCC ATCCTCTCCA CGCTGCTCTG
2581 CAGCCTGTGC TACGGCGACA TGGAGAACAA GCTGTTTGCG GGGATTCGGC GGGACGGGCT
2641 GCTCCTGCGT TTGGTGGATG ATTTCTTGTT GGTGACACCT CACCTCACCC ACGCGAAAAC
2701 CTTCCTCAGG ACCCTGGTCC GAGGTGTCCC TGAGTATGGC TGCGTGGTGA ACTTGCGGAA
2761 GACAGTGGTG AACTTCCCTG TAGAAGACGA GGCCCTGGGT GGCACGGCTT TTGTTCAGAT
2821 GCCGGCCCAC GGCCTATTCC CCTGGTGCGG CCTGCTGCTG GATACCCGGA CCCTGGAGGT
2881 GCAGAGCGAC TACTCCAGCT ATGCCCGGAC CTCCATCAGA GCCAGTCTCA CCTTCAACCG
2941 CGGCTTCAAG GCTGGAGGA ACATGCGTCG CAAACTCTTT GGGGTCTTGC GGCTGAAGTG
3001 TCACAGCCTG TTTCTGGATT TGCAGGTGAA CAGCCTCCAG ACGGTGTGCA CCAACATCTA
3061 CAAGATCCTC CTGCTGCAGG CGTACAGGTT TCACGCATGT GTGCTGCAGC TCCCATTTCA
3121 TCAGCAAGTT TGGAAGAACC CCACATTTTT CCTGCGCGTC ATCTCTGACA CGGCCTCCCT
3181 CTGCTACTCC ATCCTGAAAG CCAAGAACGC AGGGATGTCG CTGGGGGCCA AGGGCGCCGC
3241 CGGCCCTCTG CCCTCCGAGG CCGTGCAGTG GCTGTGCCAC CAAGCATTCC TGCTCAAGCT
3301 GACTCGACAC CGTGTCACCT ACGTGCCACT CCTGGGGTCA CTCAGGACAG CCCAGACGCA
```

Fig. 1a

```
3361 GCTGAGTCGG AAGCTCCCGG GGACGACGCT GACTGCCCTG GAGGCCGCAG CCAACCCGGC
3421 ACTGCCCTCA GACTTCAAGA CCATCCTGGA CTGATGGCCA CCCGCCCACA GCCAGGCCGA
3481 GAGCAGACAC CAGCAGCCCT GTCACGCCGG GCTCTACGTC CCAGGGAGGG AGGGGCGGCC
3541 CACACCCAGG CCCGCACCGC TGGGAGTCTG AGGCCTGAGT GAGTGTTTGG CCGAGGCCTG
3601 CATGTCCGGC TGAAGGCTGA GTGTCCGGCT GAGGCCTGAG CGAGTGTCCA GCCAAGGGCT
3661 GAGTGTCCAG CACACCTGCC GTCTTCACTT CCCCACAGGC TGGCGCTCGG CTCCACCCCA
3721 GGGCCAGCTT TTCCTCACCA GGAGCCCGGC TTCCACTCCC CACATAGGAA TAGTCCATCC
3781 CCAGATTCGC CATTGTTCAC CCCTCGCCCT GCCCTCCTTT GCCTTCCACC CCACCATCC
3841 AGGTGGAGAC CCTGAGAAGG ACCCTGGGAG CTCTGGGAAT TTGGAGTGAC CAAAGGTGTG
3901 CCCTGTACAC AGGCGAGGAC CCTGCACCTG GATGGGGGTC CCTGTGGGTC AAATTGGGGG
3961 GAGGTGCTGT GGGAGTAAAA TACTGAATAT ATGAGTTTTT CAGTTTTGAA AAAAA
```

Fig. 1b

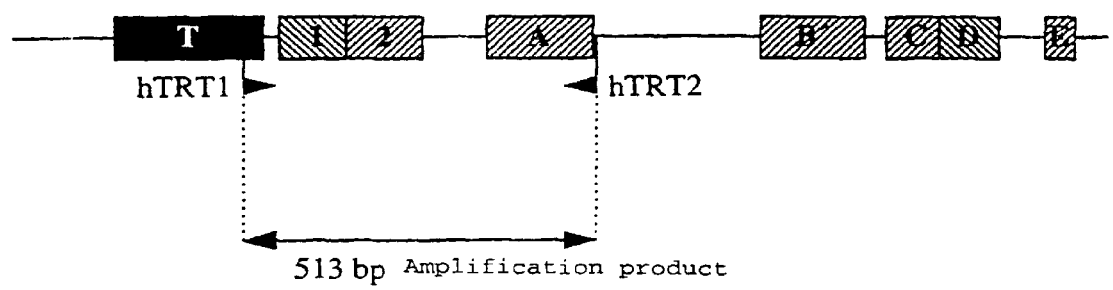
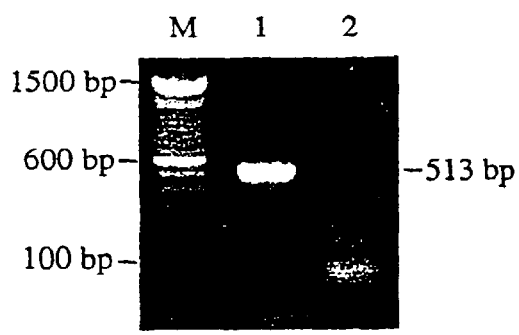
Fig. 2

Catalytic sububit of human telomerase

| Name | Sequence (5`-3) |
|---|---|
| hTRT 1 | CTACCGGAAGAGTGTCTGGAGCAAGTTGCAAAGC |
| hTRT 2 | GGCATACCGACGCACGCAGTACGTGTTCTG |
| hTRT o | CGTTCTGGCTCCCACGACGTAGTC |

T-cell receptor:

| Name | Sequence (5`-3) |
|---|---|
| TCR 1 | GAGGTCGCTGTGTTTGAGCCATCAGAAG |
| TCR 2 | GATCTCATAGAGGATGGTGGCAGACAG |

β-actin:

| Name | Sequence (5`-3) |
|---|---|
| Act 1 | GATGATGATATCGCCGCGCTCGTC |
| Act 2 | CTCAAACATGATCTGGGTCATCTTC |

β-globin:

| Name | Sequence (5`-3) |
|---|---|
| Glob 1 | ACCCAGAGGTTCTTTGAGTC |
| Glob 2 | TCTGATAGGCAGCCTGCACT |

Fig. 6

METHOD FOR QUANTITATIVELY ANALYZING TUMOR CELLS IN A BODY FLUID AND TEST KITS SUITED THEREFOR

This application is the National Stage of International Application No. PCT/EP99/00716, filed Feb. 3, 1999. Benefit of priority under 35 U.S.C. §365(b) to German Application No. 198 04 372.4, filed Feb. 4, 1998 is claimed herein.

The invention relates to a method for the quantification of tumor cells in a body fluid, in which firstly the sample to be examined is subjected to a process for the enrichment or depletion of tumor cells and a reaction is carried out on the enriched or depleted tumor cells in which the mRNA encoding the catalytic subunit of the telomerase is specifically amplified, and subsequently the amount of amplified nucleic acid is determined quantitatively, and to test kits suitable therefor.

Virtually all solid malignant tumors have the potential to form metastases. The metastasis process comprises the spread of malignant cells as micrometastases, usually via the blood or lymph to remote organs and the development of autonomous secondary tumors. The extent of metastasis determines the prognosis of an oncosis.

The requirements of tumor prevention or aftercare programs are to diagnose primary tumors or a recurrence or a metastasis early, even before metastases become clinically manifest. This aim cannot yet be satisfactorily met with the available instrumental techniques; in particular, there is still a diagnostic gray zone between the detection of circulating tumor cells and incipient formation of metastases in organs. Early diagnosis of circulating malignant cells, for example in peripheral blood of a patient undergoing tumor aftercare, would make it possible to introduce immunomodulating therapy or polychemotherapy, which is possibly curative, at an early date, that is to say even before organ metastasis becomes manifest. Quantification of the tumor cells in peripheral blood before and after the therapy represents an important control in such cases.

The life span of eukaryotic cells is, according to the telomer hypothesis, determined by the length of the termini of the chromosomal DNA, the telomers. Thus, according to this theory, telomers have the function of a mitotic clock. Because of the replication mechanism of the DNA polymerases, the telomers are shortened after each cell division by the length of the replication primer. As a consequence, after each cell division, the chromosomes are shorter, reaching a critical length after a certain number of cell divisions. The cells then proceed into a senescent phase where they no longer divide and finally die. However, in some cases this regulation mechanism can be bypassed by a ribonuclearprotein, the telomerase, and the cells become immortal. The telomerase synthesizes, at the 5'-end of the chromosomes, the telomer sequences lost during replication, where the RNA component of the protein (human Telomerase RNA component, hTR) serves as matrix and part of the protein component forms the catalytic subunit (human Telomerase Reverse Transcriptase, hTRT).

In humans, the cells with active telomerase and unlimited life expectancy are, in particular, the germ cells and the hemapoietic stem cells, which are capable of dividing during the entire life span of a person. In addition, increased telomerase activities are also found on activated human B and T lymphocytes. Besides this normal physiological role of telomerase, an increased telomerase activity is found in about 90–95% of all human tumor tissues. The telomerase activity of tumor cells can therefore form the basis for a detection system for disseminated circulating tumor cells in body fluids, which may potentially give rise to metastases.

Telomerase is a ribonucleoprotein with reverse transcriptase activity [Shippen-Lentz et al. (1990), Science 247: 546π which uses an integral RNA sequence as template for independent DNA synthesis [Greider et al. (1989). Nature 337: 331] by which new telomeric DNA are synthesized at the ends of the chromosomes. Telomeres consist of highly conserved (TTAGGG)n in tandem sequences with a length of about 5–15 kilobases (kb)/cell genome and have the task of stabilizing the chromosomes on the nuclear membrane and protect the coding genomic DNA from uncontrolled recombination and degradation [Mehle et al. (1994). Cancer Res 54: 236]. Whereas a dynamic equilibrium between shortening of the chromosome ends and de novo synthesis of telomeric sequences by telomerase is postulated in lower eukaryotes, normal human somatic cells show low or undetectable telomerase activity. In addition, telomerase is not growth-regulated, in contrast to other DNA enzymes, since none of the actively proliferating cell cultures showed detectable telomerase activity. Only germ cells and almost all tumor cell lines [Ohyashiki et al. (1994). Cancer Genet Cytogenet 78:64; Rogalla et al. (1994). Cancer Genet Cytogenet 77: 19; Schwartz et al. (1995). Cancer 75: 1094] and tumor tissues (Lunge, [Hiyama et al. (1995). Oncogene 10: 937; Shirotani et al. (1994). Lung Cancer 11: 29], kidneys [Mehle et al. (1994). Cancer Res 54: 236], ovaries [Chadeneau et al. (1995). Cancer Res 55: 2533] and blood [Counter et al. (1995). Blood 85: 2315]) show measurable telomerase activity and a constant telomere length which is retained throughout an infinite number of cell divisions. Activation of telomerase with the stabilization, associated therewith, of the telomere length can therefore be regarded as a critical step in the direction of immortalization of somatic cells.

Feng et al. were able to clone the integral RNA sequence of human telomerase (hTR), which is encoded on the distal segment (q) of chromosome 3. The authors were able to demonstrate, by competitive polymerase chain reaction (PCR), a significant increase in telomerase expression in tumor tissues and in germinal tissues by comparison with normal somatic cells [Feng et al. (1995), Science 269: 1236]. An antisense construct of the hTR sequence caused cell death (apoptosis) in transfected HeLa cells. These data demonstrate stringent repression of telomerase in somatic tissues, as well as the fact that malignant growth depends on the presence of immortal cells and on the activation of telomerase.

In 1997, Nakamura et al. characterized a protein component of the catalytic subunit of human telomerase. In comparison with the RNA component of human telomerase (hTR), the mRNA encoding the catalytic subunit of human telomerase (hTRT) correlates considerably better with the telomerase activity (Nakamura T M, Morin G B, Chapman K B, Weinrich S L, Andrews W H, Lingner J, Harley C B, Cech T R (1997): Telomerase catalytic subunit homologs from fission yeast and human. Science 277: 955–9) and is therefore more suitable for cancer diagnosis. Meyerson et al. localized hTRT on the human chromosome 5p and confirmed the strong correlation of the hTRT mRNA detection with the enzymatic activity of human telomerase (Meyerson M, Counter C M, Eaton E N, Ellisen L W, Steiner P, Caddle S D, ziaugra L, Beijersbergen R L, Davidoff M J, Liu Q, Bacchetti S, Haber D A, Weinberg R A (1997): hEST2, the putative human telomerase catalytic subunit gene, is up-regulated in tumor cells and during immortalization. Cell 90: 785–95).

Currently, the standard method for determining the catalytic activity of telomerase is the TRAP assay (Telomeric Repeat Amplification Protocol) [Kim et al. Science (1994) 266: 2011]. Here, the telomerase present in cell extract synthesizes extension products which are subsequently amplified in a polymerase chain reaction (PCR). A densitometric evaluation of the amplification products then permits quantification of the telomerase activity. Depending on the sample material, the test laboratory and the protocol used, the sensitivity of the TRAP assay was stated as being 4–100 cells/batch. Since the crude extract of lyzed cells or tissues is used in the TRAP assay, this method is highly susceptible to interference by inhibitors of the DNA polymerase used in PCR (Taq polymerase).

The TRAP assay is used, for example in WO 98/02581, for the diagnosis of precancerous or cancerous damage to the cervix, endocervix, the vagina or vulva.

WO 97/18322 discloses a method for the quantification of tumor cells in which initially a reaction is carried out with the sample to be tested where the RNA component of the telomerase is specifically amplified, and the amount of amplified nucleic acid is subsequently determined quantitatively.

WO 96/01835 likewise discloses a method for the detection of the RNA component of telomerase in cells or cell samples.

In spite of the known methods for detecting tumor cells, there is still a need for reliable and simple methods for quantifying tumor cells in body fluids.

The object of the present, invention was therefore to develop a method with which it is possible to determine tumor cells quantitatively in a body fluid.

The invention therefore relates to a method for the quantification of tumor cells in a body fluid, in which firstly the sample to be examined is subjected to a process for the enrichment or depletion of tumor cells and a reaction is carried out on the enriched or depleted tumor cells in which the mRNA encoding the catalytic subunit of the telomerase is specifically amplified, and subsequently the amount of amplified nucleic acid is determined quantitatively, and to test kits suitable therefor.

The body fluid in which the tumor cells are to be quantified can be any human or animal body fluid or a dispersion of cell tissue. It is, for example, blood, in particular peripheral blood, such as venous or arterial blood, lymph, urine, stool, exsudates, transudates, spinal fluid, seminal fluid, saliva, liquids from natural or unnatural body cavities, bone marrow and disperse body tissue. The fluids from natural body cavities can, for example, be serous fluids such as peritoneal and pleura fluids, the fluids from unnatural body cavities can, for example, be fluids from cysts.

Preferred body fluids are blood, bone marrow, lymph, serous fluids from body cavities and urine, and particular preference is given to blood and urine. Urine is particularly suitable for enriching cells from bladder tumors.

Peripheral blood is, for example, taken from the subject by puncturing an artery, vein or finger pad and, after an enrichment or depletion process, the tumor cells contained in the sample are transferred into an RNA lysis buffer which comprises, for example, urea or, preferably, guanidinium isothiocyanate, in order to denature any RNases present and to release the nucleic acids from the cells [see, for example, Chomczynski et al. (1987) Anal. Biochem. 162, 156]. The nucleic acids can be isolated from the strongly saline medium of the RNA lysis buffer, for example, by means of silica particles to which all nucleic acids are able to bind [Boom et al. (1990) J. Clin. Microbiol., 29, 495]. The particles are then washed several times with suitable buffer and the bound nucleic acids are eluted. It is subsequently advantageous to hydrolyze any genomic DNA present in the sample using RNase-free DNase in a suitable buffer, so that no false-positive results or excessive background noise result due to false amplification signals, because DNA is possibly still present, in the later amplification of the mRNA which codes for the catalytic subunit of telomerase. This is generally followed by inactivation of the DNase, for example by phenol extraction and/or heat denaturation. It is possible and advantageous, before or, preferably, after treatment of the sample with DNase, also to purify the RNA present in the sample further, for example by chromatographic methods such as ion exchange chromatography, preferably on silica gel.

To check whether possibly interfering genomic DNA is still present in the sample, it is subsequently possible to carry out an amplification reaction with the telomerase-specific oligonucleotide primers which are described hereinafter, in which case the RNA present in the sample is not transcribed to cDNA by a reverse transcription reaction beforehand. Only in the case where the sample is free of telomerase-specific DNA does no amplification take place, with the result that no amplified DNA can be measured.

This is followed by transcription of the RNA present in the sample into cDNA, generally by means of the reverse transcription reaction, for example with AMV reverse transcriptase. The method is generally known and is described, for example, in Sambrook et al., Molecular Cloning: A Laboratory Manual, New York Cold Spring Harbor Laboratory, 1989. In a preferred embodiment of the reverse transcription, it is also possible to use a thermostable RNA-dependent DNA polymerase as described in WO 90/07641. Suitable oligonucleotide primers for the reverse transcriptase are, for example and advantageously, the oligonucleotide primers described below or random primers with a particular length.

The subsequent amplification can be carried out, for example, with DNA polymerase, for example by the polymerase chain reaction (PCR) (see, for example, U.S. Pat. Nos. 4,683,195; 4,683,202; 4,965,188) or, preferably, with an RNA polymerase by, for example, isothermal nucleic acid sequence-based amplification (NASBA). Specific oligonucleotide primers derived from the nucleic acid to be amplified are required for the amplification in each case. It is possible in the present invention to use any sequence section of the cDNA coding for the catalytic subunit of telomerase for synthesizing the oligonucleotide primers. The oligonucleotide primers are preferably about 20 to about 40, preferably about 25 to 35, nucleotides long. The amplification product is generally about 100 to about 2000 bases, preferably about 200 to about 1500 bases, in particular about 450 to about 550 bases, long. The following oligonucleotide primers, which have been derived from the sequence shown in FIG. 1, are particularly preferred for the novel method:

5' CTACCGGAAG AGTGTCTGGA GCAAGTTGCA AAGC 3' (hTRT1) (SEQ ID NO. 1), and/or

5' GGCATACCGA CGCACGCAGT ACGTGTTCTG 3' (hTRT2) (SEQ ID. NO. 2), where hTRT1 and/or hTRT2 may, where appropriate, additionally comprise a promoter sequence for an RNA polymerase. The oligonucleotide primer hTRT1 corresponds to the 5' primer and hTRT2 corresponds to the 3' primer. The amplification product is 513 bp long. The primers may, for example, be prepared synthetically using the triester methods (Matteucci et al., (1981), J. Am. Chem. Soc., 103, 3185–3191). The DNA polymerase which can be used is, for example, a non-thermostable DNA polymerase such as T4 DNA polymerase, T7 DNA polymerase, E. coli polymerase I or the Klenow fragment of E. coli or, preferably, a thermostable DNA polymerase such as Taq polymerase (see, for example, U.S. Pat. No. 4,889,818).

The general principle of the PCR reaction [sic] consists of heat-denaturation of the DNA and restoration of the double strand in the presence of suitable oligonucleotide primers with opposite orientation of the single strand using DNA polymerase in several repeated reaction cycles. The cycle is then repeated until sufficient DNA has been formed for quantification by one of the methods described below. In general, about 20 to about 40 cycles, preferably about 30 to about 35 cycles, suffice.

In the NASBA method (also called 3SR system) there is use of at least one oligonucleotide primer, preferably hTRT2, which comprises a promoter for the RNA polymerase, preferably for T7 RNA polymerase [see, for example, Guatelli et al. (1990) Proc. Natl. Acad. Sci. USA, 87, 1874–1878 or Kievits et al. (1991), J. Virol. Methods, 35, 273–286]. Firstly, as already described in detail above, the RNA is transcribed with the aid of one of the oligonucleotide primers described above and of a reverse transcriptase, preferably AMV reverse transcriptase, into cDNA. The reaction product is an RNA:DNA double strand whose RNA component is then degraded by an RNase, preferably RNase H, to give a DNA single strand. Using one of the oligonucleotide primers described above, the DNA single strand is made up to the DNA double strand using a DNA polymerase. AMV reverse transcriptase is once again a suitable and preferred DNA polymerase because this transcriptase has not only an RNA-dependent DNA polymerase activity but also a DNA-dependent DNA polymerase activity. The reaction product is a DNA double strand which comprises the promoter for, for example, T7 RNA polymerase. The RNA polymerase then synthesizes an "antisense" RNA strand again, and the cycle can begin again. In general, about 20 to about 40 cycles, preferably about 30 to about 35 cycles, suffice to provide sufficient amplification product, preferably "antisense" RNA, for the subsequent quantification.

The amplification products can be quantified by, for example, staining with intercalating fluorescent dyes such as, for example, ethidium bromide and direct visualization and quantification, for example in an agarose or polyacrylamide gel under ultraviolet light.

However, since the amplification products to be quantified are in direct correlation with the amount of RNA employed only when the amplification reaction is in a linear phase, it is necessary for quantification to measure the course of the reaction of the amplification. To this end, the reaction products have to be measured after each amplification cycle, and the linear range in which quantification can be carried out with sufficient certainty is determined using the course of the reaction. Thus, it is advantageous if the amplification products are labeled even during amplification and the kinetic of the amplification is measured continuously even during the amplification process. In the case of the Taqman™-PCR (Hoffmann-La Roche), for example, this is carried out with the aid of a probe which is specific for the amplification product. At its 3' and 5' ends, the probe is labeled with different fluorescent dyes ("Reporter" and "Quencher"), and the probe is present in the reaction vessel during the entire PCR. Owing to the 5'-3'-exonuclease activity of the DNA polymerase used for amplification (AmpiTaq™, Hoffmann-La Roche), the probe is hydrolyzed during prolongation of the DNA daughter strand, and in the process, the quencher is separated from the reporter. As a consequence, the quench effect is terminated and the characteristic fluorescence emitted by the "reporter" can be measured. The intensity of this fluorescence is directly proportional to the PCR products which were amplified per synthesis cycle.

Other examples of suitable labels are radioactive labels, biotin labels, fluorescent or electrochemoluminscent (ECL) labels. In general, the labels are attached to the nucleotides as starting materials for amplification by DNA or RNA polymerase. The radiolabeled amplification products (for example PCR or NASBA products) can be detected by measuring the radioactivity, the biotin-labeled amplification products can be detected via a dye which carries avidin or streptavidin, the fluorescent-labeled amplification products can be detected with a fluorometer and the electrochemoluminscent-labeled amplification products can be detected with an ECL detector. However, the most preferred detection method is automatic in vitro hybridization, such as, for example, in the case of TaqMan™-PCR, even during the amplification process.

In contrast to "real time" quantification of PCR products as in the case of TaqMan™-PCR, it is also possible to quantify PCR products using dilution series. To this end, the RNA or the corresponding cDNA is employed in various dilutions. This gives, similar to the "real time" quantification, a sigmoidal reaction kinetic where once more in the linear range the amplification products are proportional to the starting material. The PCR products are detected with the aid of fluorescent-dye-labeled or radiolabeled deoxy-nucleotides which are incorporated directly into the PCR products by DNA polymerase during amplification. Furthermore, oligonucleotides (so-called primers which are required in the PCR for initializing the synthesis of the daughter strand and which are present in all amplification products incorporated at the 5' and 3' end of the DNA after PCR) are labeled with certain molecules (for example biotin) to immobilize the amplification products after PCR with the aid of specific antibodies or streptavidin. This immobilization can be carried out, for example, in a microtiter plate, in which, subsequently, a color reaction can take place with the aid of a molecular-labeled specific probe which hybridizes with the amplification products and with the aid of an enzyme-coupled (for example peroxidase-coupled) antibody against the marker molecule of the probe. This color reaction can subsequently be evaluated photometrically.

The oligonucleotide for detection by in vitro hybridization generally carries the labels described above, and in connection with the NASBA amplification method the hybridization probe carries an electrochemoluminsecent label, preferably a tris[2,2-bipyridine]ruthenium[II] complex label [see, for example, van Gemen et al. (1994), J. Virol. Methods, 49, 157–168].

Accurate and sensitive quantification of the amplification products can also advantageously be achieved by coamplification of a defined amount of one or more known nucleic acids (standard nucleic acids) [see, for example, van Gemen et al. (1993), J. Virol. Methods, 43, 177–188]. In this case, a different but exactly known amount of the coamplifying standard nucleic acid or nucleic acids is added, for example in the form of a dilution series, to the unknown amounts of the sample to be investigated, and the amplification products of the sample and one or more coamplifying standard nucleic acids are determined quantitatively in independent mixtures. Comparison of the measured results reveals the amount of the mRNA coding for the catalytic subunit of telomerase to be determined in the sample.

It is advantageous to amplify the coamplifying standard nucleic acid or nucleic acids with the same oligonucleotide primer as the sample to be investigated and the amplification products also have essentially the same length. It is particularly preferred for the coamplifying nucleic acids to have the same sequence as the amplification product of the sample to be determined, with the exception of about 20 nucleic acids between the oligonucleotide primer binding sites, which have an arbitrary but known sequence. It is possible thereby to quantify, independently of one another, the amplification product to be determined in the sample from the coamplifying amplification, product, for example by a hybridization as described in detail, for example, in Sambrook et al. (supra), using appropriately complementary labeled oligonucleotides. It is particularly advantageous if several, preferably three, different coamplifying nucleic acids are added in different concentrations to the sample, because this makes it possible to reduce the number of individual amplification reactions which would otherwise have to be carried out [see van Gemen et al. (1994) J. Virol. Methods 49, 157–168]. It is also particularly preferred to add the coamplifying nucleic acids to the RNA lysis buffer described above because it is possible thereby to exclude the effect of possible nucleic acid losses in the subsequent workup of the sample.

Suitable and advantageous coamplifying standard nucleic acids in the present invention are RNA single stranded sequences which are prepared by in vitro transcription, for example with Sp6 or T7 RNA polymerase, from constructs which comprise the DNA or cDNA of the sample to be amplified and which are in each case provided with a randomized exchange of a sequence of, for example, about 10 to about 30, preferably about 20, nucleotides.

The constructs preferably consist of a transcription vector having a binding site for Sp6 or T7 RNA polymerase between a "multiple cloning site" in which the DNA or cDNA of the sample to be amplified has been cloned. The cloned sequence can be opened by selective hydrolysis with restriction endonucleases, preferably with two different restriction endonucleases, and a fragment of a defined length can be cut out and replaced by a fragment of equal length, for example using T4 ligase. The cloned fragment may comprise replacement of a sequence of any length, for example about 10 to about 30, preferably about 20, nucleic acids and is preferably located between the oligonucleotide primer binding sites. This procedure can be repeated in order to insert other nucleic acid sequences at the same site. If no suitable cleavage sites can be found, for example because the vector is also cut, it is necessary to create artificial cleavage sites. This can take place, for example, by recombinant PCR which is described in essence by Higuchi et al. [Higuchi, R. (1988). Nucleic Acid Res: 16: 7351–7367; Higuchi, R. (1990). M. Innis A. et al. eds. San Diego, New York, Berkley, Boston, London, Sydney, Tokyo, Toronto, Academic Press, Inc. 177–183] and in the experimental part of the present invention.

Preferably used for the purpose of the invention are in vitro transcribed RNA single stranded sequences of constructs which
a) comprise the entire cDNA corresponding to the mRNA which codes for the catalytic subunit of human telomerase and
b) in which a randomized exchange of a sequence of about 20 nucleotides has been introduced.

Since the standard nucleic acids (for example, hTRTKa, hTRTKb and hTRTKc) differ from one another and from the wild-type sequence for example only by a randomized and known sequence which is 20 base pairs long, the amplification products of the standard nucleic acids and of the wild-type sequence can be detected by complementary binding of labeled oligonucleotides in four separate mixtures.

The corresponding reverse complementary sequences are used to detect the amplified "antisense" RNA.

After this, the individual amplified amounts of the wild-type and standard nucleic acids are determined. The unknown initial amount of the wild-type sequence can be calculated by comparing with the different amplified amounts of the standard nucleic acids when the initial amount is known (for example hTRKa: $10^2$, hTRKb: $10^4$ and hTRKc: $10^6$ molecules). It is then possible to conclude from this the number of metastases for the removed body fluid.

As internal positive control of the method and of the sample to be investigated it is possible additionally to amplify and detect a nucleic acid which generally always occurs in a body fluid. Examples of suitable nucleic acids are the mRNA coding for β-globin or for glyceraldehyde-phosphate dehydrogenase (GAPDH) (see, for example, GB 2 260 811) which always occur in the cells of the body fluid. Suitable oligonucleotide primers for human β-globin mRNA are, for example, primers with the sequences:
5' ACCCAGAGGT TCTTTGAGTC 3' (Glob 1) (SEQ ID. NO. 3) and
5' TCTGATAGGC AGCCTGCACT 3' (Glob 2) (SEQ ID. NO. 4)

Further internal positive controls of the method and of the sample to be investigated can additionally be cell-specific nucleic acids, such as β-actin mRNA, with the primers (Nakajima-Iiji, S., Hamada, H., Reddy, P., Kakanuga, T. (1985): Molecular structure of the cytoplasmatic β-actin gene: Interspecies homology of sequences in the introns. Proc Natl Acad Sci USA 82, 6133–7):
5' GATGATGATATCGCCGCGCTCGTC 3' (Act 1) (SEQ ID. NO. 5)
5' CTCAAACATGATCTGGGTCATCTTC 3' (Act 2) (SEQ ID. NO.6)
or T-cell-specific nucleic acids, such as the mRNA of the T-cell receptor, with the primers (Toyonaga, B., Yoshikai, Y., Vadasz, V., Chin, B., Mak, T. W. (1985): Organization and sequences of the diversity, joining, and constant region of the human T-cell receptor β chain. Proc Natl Acad Sci USA 82, 8624–8):
5' GAGGTCGCTGTGTTTGAGCCATCAGAAG 3' (TCR 1) (SEQ ID. NO. 7)
5' GATCTCATAGAGGATGGTGGCAGACAG 3' (TCR 2) (SEQ ID. NO. 8)

To prevent or reduce false-positive results or so-called background noise which is caused by telomerase activities which are possibly present in nontumor cells, the sample to be investigated is, according to the invention, initially subjected to a process for enrichment or depletion of tumor cells. To this end, it is advantageous to either purify the body fluid sampled, by appropriate methods or to cultivate it under conditions which are unfavorable for the contaminating telomerase-positive nontumor cells but favorable for the tumor cells present.

In the case of purification, in particular from the sample to be investigated, stem cells and/or activated immune cells should be depleted or tumor cells concentrated. Since, in general, the individual cells have specific surface markers, removal or concentration of the cells by immunoabsorption is particularly advantageous. Examples of suitable methods are magnetic (MACS) or fluorescence-activated (FACS) cell sorting [see, for example, B. Göttlinger & Radbruch (1993) mta, 8, 530–536, No. 5]. Thus, for example hemapoietic stem cells can be removed from the blood sample by means of MACS via their CD34 surface marker (Kato & Radbruch (1993) Cytometry, 14, 384–392]. B cells can be removed, for example, via their CD10, CD19 and/or CD20 surface markers, and T cells via CD45RA and/or CD7. Tumor cells can be concentrated via their specific tumor markers, for example CEA. Besides MACS or FACS, also particularly suitable for depletion or concentration of the relevant cells are antibodies against the specific surface markers, which are bound in particular to commercially available magnetic beads (for example Dynabeads M450, Dynal Corp.).

Mononuclear cells can be isolated by the following methods:

specific lyzes of the erythrocytes (for example ammonium chloride/hypertonic shock), specific lyzes of mononuclear blood cells (for example L-leucyl-L-leucine methyl ester for monocytes and cytotoxic cells), negative/positive selection via specific surface markers (for example negative: CD 4, 8, 34, etc.; positive: Ber-EP4, AUA1, CEA), density gradient centrifugation of euploid vs. aneuploid cells or density gradient centrifugation of mononuclear annuclear cells (for example Ficoll).

In the 60s and 70s, when methods such as, for example, FACS or MACS were still unavailable, tumor cells of hematopoetic cells were separated based on their differing density (J. A. Fleming et al., J. clin. Path. (1967), 20, 145). According to this data, tumor cells have a specific density of 1.040–1.080, whereas erythrocytes and polymorhnuclear leukocytes have a higher density. In contrast, lymphocytes have a specific density in the range from 1.060–1.075, thus overlapping with the specific density of tumor cells. Thus, complete removal of the likewise telomerase-active lymphocytes from the tumor cells via their differing densities should not be possible. Consequently, use of a standard solution for isolating lymphocytes, such as, for example, Histoprep® of a density of 1.077 g/ml showed that lymphocytes of healthy blood donors of a density of up to 1.077 g/ml have telomerase activity.

For a particularly preferred embodiment of the method according to the invention, it has now been found that the tumor cells can be concentrated by covering a cell separation medium of a density in the range from 1.055 to <1.070 g/ml with a layer of the body fluid which contains the tumor cells, followed by centrifugation. By using the specific cell separation medium, the cells which are present in the body fluid are separated such that the lymphocytes which are, owing to their density, concentrated together with the tumor cells have no telomerase activity.

In the concentration process, a cell separation medium is used as discontinuous gradient, which is covered with a layer of the body fluid. By centrifugation, the cells are separated according to their specific cell density and can be collected in individual fractions. The specific density of the cell separation medium permits virtually complete separation of tumor cells from the corpuscular fractions present in body fluids, specifically from the cells of the red and white blood system. In addition, the method permits the separation of telomerase-positive from telomerase-negative hematopoietic cells, where the concentrated tumor cells are, after centrifugation, in the same fraction as the telomerase-negative hematopoietic cells, so that a subsequently detected telomerase expression in this fraction can be assigned without any doubt to the tumor cells present.

It is also surprising that the reduction of the density of the cell separation medium, which is slight compared with the prior art, permits the number of contaminating blood cells to be reduced considerably. As a consequence, the total cell count is reduced significantly without any significant loss of tumor cells, which makes, for example, screening of microscopic preparations considerably easier and, on a clinical scale, possible in the first place.

It has been found that a particularly good separation performance is achieved using a cell separation medium of a density in the range from 1.060–1.067 g/ml, more preferably 1.060–1.065 g/ml and particularly preferably about 1.065 g/ml.

The centrifugation is advantageously carried out at about 1000×g for about 30 minutes. The temperature during the centrifugation is preferably about 4° C. It has been found to be particularly advantageous to carry out the centrifugation using slow acceleration and no braking, so that the cell separation medium and the body fluid at the beginning of the centrifugation or the fractions at the end of the centrifugation are not mixed with one another.

The cell separation medium used can, in principle, be any suitable liquid of the desired density. The cell separation medium should not react with the body fluid or the cells contained therein. Advantageously, use can be made of, for example, Ficoll or Percoll, where the solutions are adjusted to the desired density, in each case following the instructions of the manufacturer. The amount of the Percoll stock solution to be diluted, having a density of 1.13 g/ml, which is required for preparing 100 ml of a Percoll work solution of the desired density (dd) is calculated, for example, according to the formula:

$$100 \text{ ml} \times (dd - 0.106 - 0.9)/10.13.$$

In each case, 10% of the Percoll work solution of the desired density consists of a 1.5 M NaCl solution, to ensure physiologic osmolarity. The difference between the amount of Percoll stock solution (density 1.13 g/ml) calculated using the above formula and the salt solution is then filled up with water to give 100 ml.

Thus, a Percoll work solution of a density of 1.060 g/ml can be prepared, for example, as follows:

41.54 ml of the Percoll stock solution (density of 1.13 g/ml)
48.46 ml of $H_2O$
10.00 ml of 1.5 M NaCl
100.00 ml of Percoll work solution, dd 1.060 g/ml The densities stated are based on a temperature of 20° C. The work solutions are advantageously prepared at room temperature and checked, for example with the aid of marker beads of a defined density.

If the body fluid used is peripheral blood, this is advantageously drawn in an anticoagulant substance and, before covering the layer of cell separation medium, diluted with a diluent. Preferred anticoagulant substances are EDTA or citrate; a suitable diluent is, for example, PBS. The blood is preferably diluted in a ratio of about 1:1. Suitable peripheral blood is venous or arterial blood.

For concentrating the tumor cells, the body fluid to be investigated is collected or drawn in accordance with customary standard protocols. Depending on the type of body fluid, it is then either initially diluted with a diluent, preferably a buffer, or it is used directly, undiluted to cover the layer of cell separation medium in a centrifugation vessel. Alternatively, it is possible to centrifuge the body fluid beforehand at, for example, 1000×g for about 10 min and, after resuspending the cells in a buffer, to cover the layer of cell separation medium. The preferred buffer is Dulbecco PBS. A suitable centrifugation vessel is, in particular, a siliconized centrifugation vessel, preferably of plastic, having a capacity of, for example, 1–500 ml. It should be possible to close the centrifugation vessel.

In a further preferred embodiment of the concentration method, one or more substances which inhibit aggregation of platelets with tumor cells are added to the body fluid prior to covering the cell separation medium. These substances can be added, for example, together with the buffer used as diluent. Suitable substances for preventing an undesirable aggregation of platelets with tumor cells are, for example, EDTA, citrate and ACD-A (acid citrate dextrose). Additionally or alternatively, the body fluid can be freed, before the cell separation medium is covered, from substances which promote aggregation of platelets with tumor cells. These are, for example, ions, such as magnesium and calcium ions.

In the centrifugation vessel, the cell separation medium, having a higher density than the body fluid to be investigated, is initially charged and subsequently covered with the body fluid. Depending on the dimensions of the centrifugation vessel and the volume of the body liquid from which the tumor cells are to be concentrated, the volume of the cell separation medium to be charged initially can be, for example, 1–250 ml.

It has been found to be particularly advantageous to cool the lower quarter of the centrifugation vessel after centrifugation and before the interphase enriched with tumor cells is drawn off intensively for a short period of time to prevent cell contamination. For example, erythrocytes and leukocytes which are present in the cell pellet an be immobilized by cooling the lower quarter of the centrifugation vessel intensively in liquid nitrogen for 5–10 minutes. Here, interphase refers to the transition between the cell separation medium and the supernatant body fluid. The tumor cells are concentrated in this interphase and, after centrifugation, collected, for example by siphoning off this phase. The intensive cooling of the centrifugation vessel prevents mixing of the cells from the different phases, which excludes false-positive test results.

To ensure that the operations proceed as smoothly as possible, the centrifugation can be carried out in a vessel which is divided into an upper and a lower compartment by a porous barrier, a filter or a sieve, hereinbelow referred to as porous barrier or barrier, where the cell suspension medium is initially charged in the lower compartment and the body fluid is introduced into the upper compartment. This prevents mixing of the body fluid to be investigated, in the upper compartment, with the cell separation medium, in the lower compartment, before and after the centrifugation step.

The position of the porous barrier in the centrifugation vessel can be chosen such that the fluid level of the cell separation medium is either exactly below, exactly within or exactly above the porous barrier.

The porous barrier can, for example, have a thickness of 1–10 mm, preferably about 5 mm. In addition, the porous barrier should be strong enough to resist the centrifugation forces without suffering any damage.

Preference is given to using barriers having a porous nature which is such that, during centrifugation, liquid and the corpuscular components of blood, such as the cells of the red and white blood system, but not the tumor cells, can pass the porous barrier unhindered. As a consequence, the cell separation medium is, during centrifugation, forced through the porous membrane into the upper compartment and the tumor cells and platelets come to rest on a level above the barrier. Particularly suitable for this purpose are porous barriers having a pore size of 20–100 $\mu$m, preferably 20–30 $\mu$m.

The porous barrier can be of any suitable material. Suitable materials are, for example, plastic, metal, ceramic or a mixture or special alloy of these substances. However, it is also possible to use any other natural or synthetic suitable material.

In a further preferred embodiment, the porous barrier is made of a hydrophobic material or is coated with a hydrophobic material.

With the aid of the porous barrier, the body fluid to be investigated can be filled into the centrifugation vessel without any mixing with the cell separation medium below which might negatively affect or prevent the concentration.

After the centrifugation, the tumor cells present in the body fluid are in the interphase of the upper compartment of the centrifugation vessel. About 80% of the fluid above the interphase can then be siphoned off carefully and discarded. If, for example, the body fluid used is blood, this residual fluid is a plasma/PBS mixture which contains the serum proteins. The remaining supernatant above the barrier, which contains the tumor cells, can then be collected and, for example, transferred into a fresh centrifugation vessel (preferably made of siliconized plastic and having the same capacity by volume as the centrifugation vessel used beforehand). When the remaining supernatant is removed, the porous barrier prevents any mixing of the cells of the upper and the lower compartment.

Advantageously, the upper compartment of the centrifugation vessel is then, for example, washed twice with a buffer, and this is like wise transferred into the fresh centrifugation vessel. Suitable buffers are, for example, Dulbeccos PBS (3.9 mM EDTA, pH 8.0, without calcium and magnesium) or NaCl/10% ACD-A (Guidelines for the collection, processing and storage of human bone marrow and peripheral stem cells for transplantation, prepared by the BCSH Blood Transufsion Task. Transfus. Med. 1994; 4: 165–72) or NaCl/5% ACD-A/1% albumin). After a further centrifugation, for example, at 1000×g at a temperature of about 4° C. for about 10 min, the collected cells can be subjected, for example, to the tumor cell detection methods.

To render the cell ring at the interphase between cell separation medium and body fluid, which is obtained after the centrifugation and which contains the tumor cells, more visible for removal from the centrifugation vessel, it has been found to be advantageous to add a dye to the cell separation medium. It is possible to add, for example, 80 $\mu$l of a 5% Trypan Blue solution to 100 ml of a Percoll work solution.

However, if a centrifugation vessel having a porous barrier is used, once the supernatant residual fluid above the interphase has been removed, preference is given to remove not only the interphase but the entire residual fluid above the porous barrier, not only because there are further cells between interphase and porous barrier but also because the cells present in the cell ring can easily be mixed by removal. To avoid losing cells from the upper compartment, this is advantageously washed twice with buffer (for example PBS).

With the concentration step, it is possible to concentrate circulating tumor cells and in particular circulating tumor cells of solid tumors, i.e. non-hematological tumors, or hematological tumor cells, i.e. tumor cells of the red and white blood system.

Using the concentration method, tumor cells can, owing to their differing density, be separated virtually completely from the corpuscular components of body fluids, such as, for example, the cells of the red and white blood system, be concentrated, and then subjected to the next step of the quantification method according to the invention.

The concentration method described has the advantage that telomerase-positive hematopoietic cells can be removed in a simple and safe manner from the tumor cells to be concentrated, so that, in the subsequent quantification step, no false-positive results by telomerase-active nontumor cells are obtained. In addition, the concentration and isolation of the tumor cells from body tissue requires only a few operations, thus making possible processing of relatively large amounts of sample material. Compared to, for example, the use of specific antibodies and subsequent separation by suitable apparatus, the costs for the materials required are significantly lower.

In addition, investigation of 10 different cell lines derived from tumor tissue, such as melanoma, prostate, breast, lung, liver and colorectal carcinoma, showed that the cells of all these cell lines are, in their majority, concentrated by the concentration process described.

In an alternative procedure for separating the blood cells in Ficoll or Percoll, the cells contained in the sample can be cultivated under conditions which are unfavorable for the contaminating telomerase-positive nontumor cells but favorable for the tumor cells present. The result of this cultivation method is that contaminating telomerase-positive nontumor cells die, whereas the tumor cells present survive.

To this end, for optimizing the cell culture, to favor, on the one hand, the proliferation of the tumor cells and, on the other hand, blood cells entering the $G_0/G_1$ phase, or their apoptosis, to concentrate metastasizing tumor cells present, the sample can be subjected to the following conditions:
selection of suitable culture media using (autologous) sera, duration of cultivation,
selection of optimum oxygen/carbon dioxide content,
addition of tumor cell/epithelial cell specific growth factors (for example EGF etc.) or
selection of a suitable surface coating to increase adherence of the tumor cells in cell culture containers and selection of adherent cells over suspended cells.

Thus, for example, cultivation can be carried out as follows:

All or aliquots (for example on microtiter plates) of the cells contained in the sample can be cultured with or without additives. Subsequently, these cultures can be subjected to influences under which nontumor cells die, but tumor cells survive. These influences can, for example, be simply the duration of the cultivation, internal (for example increase or decrease of the pH in the culture medium) or external influences (such as, for example, increase or decrease of $pCO_2$ or $pO_2$). Our investigations have shown, for example, that even during a simple cultivation of whole blood at 37° C. for 5 days the mRNA coding for the catalytic subunit of human telomerase (hTRT) was no longer detectable between day 1 and day 2. However, the mRNA for the T cell receptor (TCR) (3 days) and β-actin (5 days) was still detectable (see FIG. 4).

In addition, cultivation by the abovementioned methods of nontumor cells and tumor cells contained in the fluids can be carried out both before and after separation of the cells from the body fluid (for example after gradient centrifugation with, for example, Fiquoll-Hypaque).

It is also particularly advantageous, alone or in conjunction with the purification or cultivation methods described above, to compare the amount of mRNA which codes for the catalytic subunit of telomerase from venous blood with the amount of mRNA which codes for the catalytic subunit of telomerase from arterial blood, since it is possible to detect, for the purpose of tumor cell determination, only about 20% of all cells in venous blood samples, compared with 100% of the cells in arterial blood samples [Koop, S. et al. (1995) Cancer Res. 55, 2520–2523]. It is likewise suitable to compare blood from the finger pulp with venous or arterial blood.

Quantitative determination of the mRNA which codes for the catalytic subunit of telomerase in the sample makes it possible to determine whether tumor cells, especially metastases, in particular micrometastases, of malignant tumors are present in the body fluid, and in what quantity. This is of great use in particular for early clinical diagnosis of the formation of metastases from malignant tumors and for monitoring tumor therapy. Tumor cells which can be detected with the present invention are, in particular, tumor cells from metastases, preferably micrometastases, from malignant tumors, especially cells from metastasizing tumors and/or neoplasms which are derived, for example, from a T-cell lymphoblastoma, T-cell leukemia cells, chronic myeloid leukemia cells, acute lymphatic leukemia cells, chronic lymphatic leukemia cells, teratocarcinoma, melanoma, carcinoma of the lung, large bowel cancer, breast cancer, hepatocellular carcinoma, kidney tumor, adrenal tumor, prostate carcinoma, neuroblastoma, brain tumor, small-cell carcinoma of the lung, rhabdomyosarcoma, leiomyosarcoma and/or lymphoma.

The present invention further relates to the oligonucleotide primers with the sequence
5' CTACCGGAAG AGTGTCTGGA GCAAGTTGCA AAGC 3' (hTRT1) (SEQ ID. NO. 1) and/or
5' GGCATACCGA CGCACGCAGT ACGTGTTCTG 3' (hTRT2) (SEQ. ID. NO. 2),
where hTRT1 and/or hTRT2 may, where appropriate, additionally comprise a promoter sequence for an RNA polymerase;
and an oligonucleotide with the sequence
5' CGTTCTGGCT CCCACGACGT AGTC 3' (hTRT o) (SEQ ID. NO. 9)
and the corresponding reverse complementary sequences of the oligonucleotide for detecting the amplified "antisense" RNA.

The invention additionally relates to a kit for quantifying tumor cells in a body fluid, for example blood, urine or else stool, exudates or transudates from body cavities, especially peripheral blood, comprising
(a) oligonucleotide primer pair for specific amplification of telomerase-encoding nucleic acid, where the oligonucleotide primer pair preferably has the following sequences:
5' CTACCGGAAG AGTGTCTGGA GCAAGTTGCA AAGC 3' (hTRT1) (SEQ ID. NO. 1) and/or
5' GGCATACCGA CGCACGCAGT ACGTGTTCTG 3' (hTRT2) (SEQ. ID. NO. 2),
where hTRT1 and/or hTRT2 may, where appropriate, additionally comprise a promoter sequence for an RNA polymerase.

In a further embodiment, the kit according to the invention additionally comprises (b) a nucleic acid or nucleic acids for co-amplification, preferably 3 RNA standard nucleic acids for co-amplification.

The novel kit may also comprise in addition, as described in detail above, a labeled oligonucleotide as hybridization probe for specific detection of the amplified cDNA of the wild-type sequence and/or several labeled oligonucleotides as hybridization probe for specific detection of the amplified cDNA of the standard nucleic acid or nucleic acids. In addition, a novel kit for PCR amplification may additionally comprise the enzymes described in detail above, where appropriate labeled nucleotides and/or suitable buffers, such as, for example, a reverse transcriptase, preferably an AMV reverse transcriptase, a DNA polymerase, preferably a Taq polymerase and/or a DNase and, where appropriate, means suitable for depletion of stem cells and/or activated immune cells and/or for concentration of tumor cells, as described in detail above.

Another novel kit for NASBA amplification [sic] may likewise comprise, besides the standard nucleic acids described in detail above, a labeled oligonucleotide as hybridization probe for specific detection of the amplified "antisense" RNA of the wild-type sequence and/or several labeled oligonucleotides as hybridization probe for specific detection of the amplified "antisense" RNA of the standard nucleic acid or nucleic acids. It may additionally likewise comprise the enzymes described in detail above, where appropriate labeled nucleotides and/or suitable buffers, such as, for example, a reverse transcriptase, preferably an AMV reverse transcriptase, an RNA polymerase, preferably a T7 RNA polymerase, an RNase H and/or a DNase, and, where appropriate, means suitable for depletion of stem cells and/or activated immune cells and/or for concentration of tumor cells, as described in detail above.

The following examples and figures are intended to describe the present invention in detail without, however, restricting it thereto.

DESCRIPTION OF THE FIGURES

FIG. 1 shows the sequence described by Nakamura et al., (SEQ ID. NO. 10) encoding the catalytic subunit of human telomerase, of 4015 base pairs (bp), and the position of the designed oligonucleotide primers or the oligonucleotide probe (hTRT o) (SEQ ID. NO. 9; underlined): 5' primer hTRT1 (position 1780–1813) (SEQ ID. NO. 1), 3' primer hTRT2 (position 2261–2290) (SEQ ID. NO. 2) with an amplification product of 513 base pairs (bp) and the probe hTRT o (position 1964–1987) (SEQ ID. NO. 9).

FIG. 2 shows (A) a diagram of the genomic organization of human telomerase (hTRT). The telomerase protein has a telomerase-specific region (T, labeled black) and has homologies to conserved regions of the reverse transcriptases of different viruses (1, 2 and A to E, hatched). The primer pair used (hTRT1, hTRT2) is indicated by arrows and is localized in a region which does not have any homologies with viral reverse transcriptases. (B) shows an agarose gel electrophoresis of an RT-PCR amplification with hTRT-specific primers on RNA of the human teratocarcinoma cell line Tera2. Band M: marker, band 1 RT-PCR amplification, band 2: the corresponding DNA control without reverse transcriptase reaction.

FIG. 6 shows the sequences of the oligonucleotides used here.

FIG. 7 shows a flow chart for the method according to the invention.

EXAMPLES

Unless noted otherwise, the following examples were carried out by standard methods as described, for example, by Sambrook, J. et al. (1989) supra, or in accordance with the instructions of the manufacturers of the kits and enzymes used.

1. Tumor Cell Concentration 1.1 General Procedure

In a siliconized centrifugation vessel made of plastic, venous blood (5–20 ml) was admixed with EDTA (final concentration 3.9 mM, pH 8.0) and mixed with 1 volume of PBS. The blood/PBS mixture was then applied to 5–10 ml of Percoll of a density of 1.065 g/ml and, with slow acceleration and without brake, centrifuged at 1000×g and 4° C. for 30 min. The lower quarter of the centrifugation vessel was subsequently incubated in liquid nitrogen for 5–10 min. This prevented contamination with cells of the pellet during the siphoning off of the cells which were located on the interphase in the transition between the Percoll and the supernatant plasma/PBS mixture. The cells of the interphase, which were mainly platelets and tumor cells circulating in the blood, were then transferred into a new siliconized centrifugation vessel made of plastic and centrifuged at 1000×g and 4° C. for 10 min. For the RT-PCR investigation that followed, the cell platelet was taken up in a guanidinium isothiocyanate buffer, as a result of which the cells were lyzed and could be subjected to RNA isolation.

1.2 Spiking Experiment

Using so-called spiking experiments, where the tumor cells of different cell lines are mixed with the blood of normal donors and the tumor cells are subsequently reisolated and investigated in the RT-PCR, it was shown that, depending on the cell line used, the telomerase activity of about 1–4 spiked tumor cells/ml of blood can be detected.

To this end, the cells of the tumor cell lines to be spiked were cultivated to confluence according to the instructions of the manufacturer (ATCC, *American Tissue Cell Culture*). The cells were then tryptanized and washed in medium (RPMI 1640). A 10 µl aliquot was removed and mixed 1:1 with Tryptan Blue, and the living cells were then determined in a counter and the corresponding cell concentration was calculated. The cell suspension was then diluted and a volume corresponding to a certain cell count was mixed with blood of healthy blood donors. Blood without any added tumor cells was used as control. The spiked tumor cells were concentrated once, for comparison, with a cell separation medium of a density of 1.070 g/ml, and according to the inventive method. To determine the recovery rate, microscopic, flow-cyteometric and RT-PCR analyses were then carried out.

a) Comparative Experiment

Figure 8:
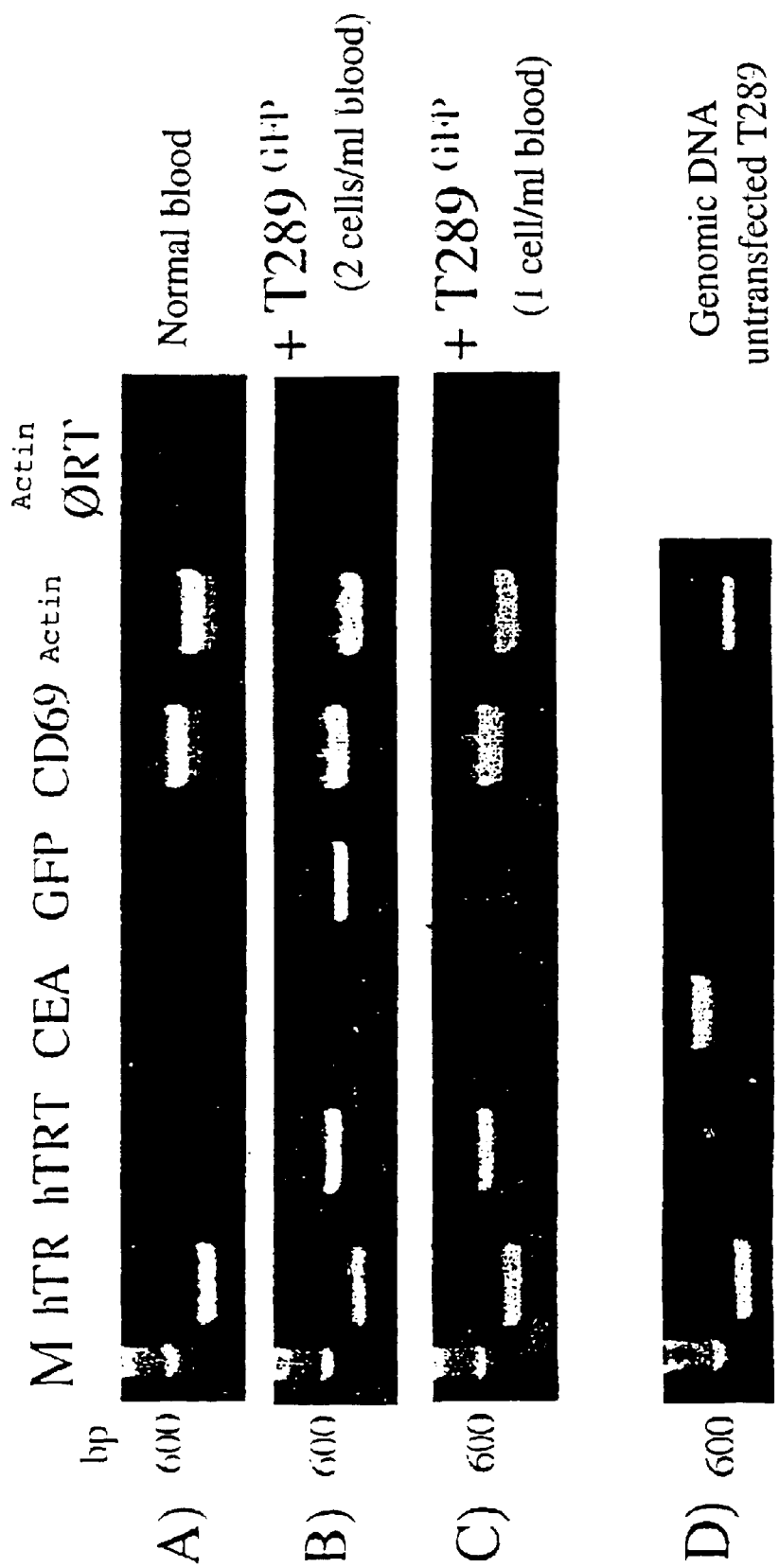
FIG. 8 shows the result of an RT-PCR analysis of blood of a healthy donor (A) and blood of the same donor mixed with GFP-transfected cells of the melanoma cell line T289 (B, C) after tumor cell concentration using a cell separation medium of a density of 1.070 g/ml.

FIG. 8 shows the result of an RT-PCR analysis of 20 ml of blood of a healthy donor (A) and 20 ml of blood of the same donor mixed with GFP-transfected cells of the melanoma cell line T289 (B, C). The blood was supplied as upper layer onto Percoll of a density of 1.070 g/ml and centrifuged, and the cells were then analyzed. In normal blood, the catalytic subunit of telomerase (hTRT) cannot be detected (A), whereas hTRT is detectable in the case of 1 and 2 spiked melanoma cells per ml of blood (B, C). However, at the Percoll density of 1.070 g/ml used, there is still a sufficiently high number of telomerase-active leukocytes in the interphase, so that the RNA component (hTR) can be detected even in unspiked blood. The presence of activated and, as a consequence, probably also telomerase-active leukocytes in the fraction of the isolated cells is also confirmed by the fact that CD69, an early activation marker in B and T cells, can be detected in all blood samples (A–C). The tumor marker CEA (Carcinoembrionic Antigene) is negative both in unspiked and in spiked blood (A–C). GFP (Green Fluorescent Protein), which was used as additional marker for the spiked tumor cells, cannot be detected in unspiked blood (A). Since only about 50% of the transfected T289 melanoma cells express GFP, the protein can only be detected in up to 2 spiked tumor cells per ml of blood (B). Actin served as RT-PCR positive control (actin) and, in the experiment without RT reaction, as negative control (actin ØRT). The PCR amplification of genomic DNA of untransfected T289 cells with the specific primer pairs for hTRT, GFP and CD69 does not give rise to any amplification products.

b) Experiment According to the Invention

Figure 9:
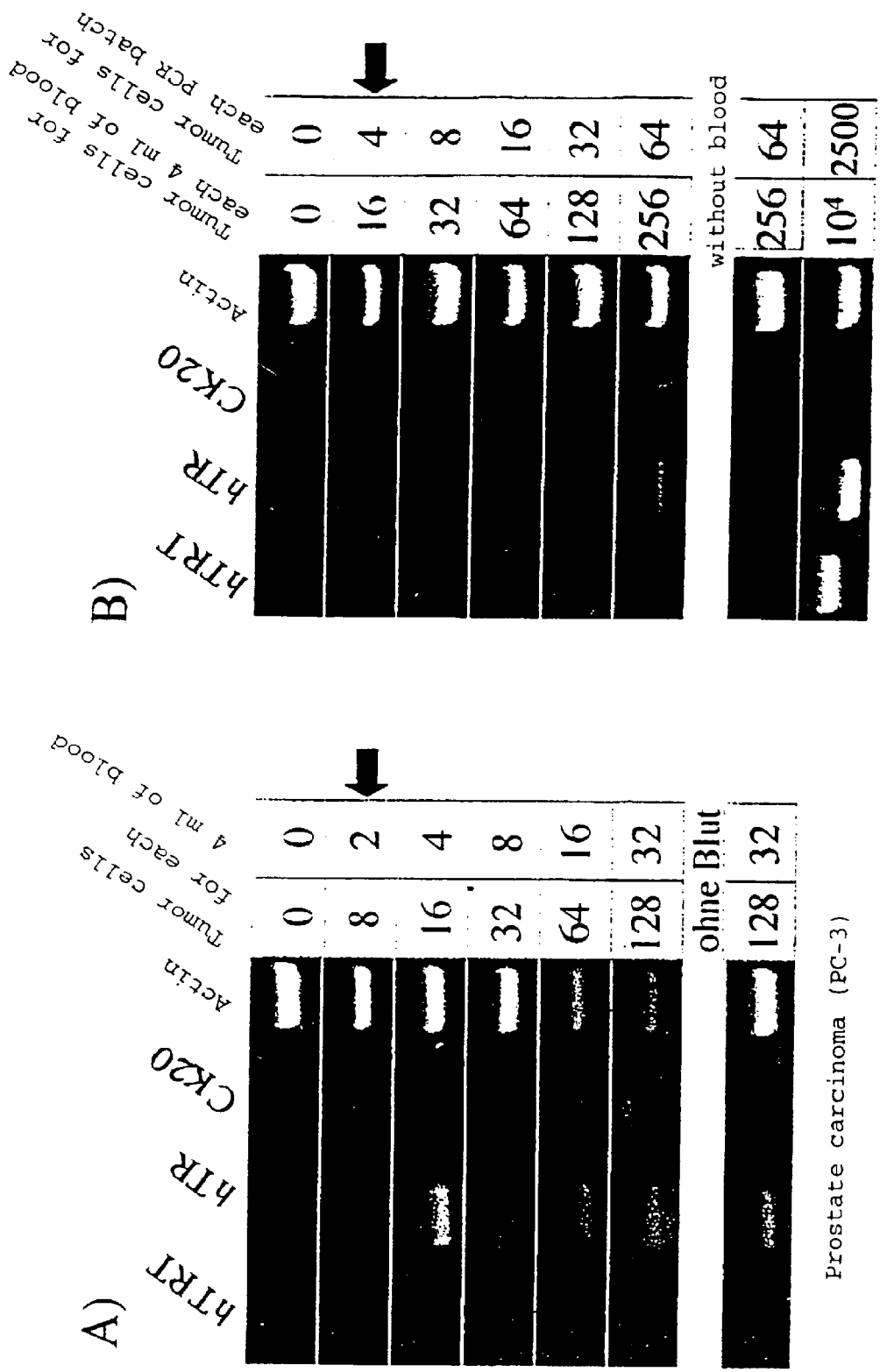
FIG. 9 shows the result of an RT-PCR analysis of blood of healthy donors which had been mixed with tumor cells of a prostate carcinoma (A) and mamma carcinoma cell line (B), after tumor cell concentration using a cell separation medium of a density of 1.065 g/ml.

FIG. 9 shows RT-PCR analyses of the blood of healthy donors which had been mixed with tumor cells of a prostate carcinoma (A) and mamma carcinoma cell line (B), applied as upper layer onto Percoll of a density of 1.065 g/ml, centrifuged and then analyzed. In contrast to when Percoll of a density of 1.070 g/ml was used, the RNA component of the telomerase (hTR) can not be detected in the unspiked blood (cf. FIG. 1). hTR can be detected in the samples with 2 spiked prostate carcinoma cells (A) and with 4 spiked mamma carcinoma cells (B) per ml of blood (black arrow). In contrast to the melanoma cell line T289, an expression of the catalytic subunit (hTRT) could not (A) be detected in these tumor cells, or only at $10^4$ tumor cells (B). Neither the prostate-cell-specific marker PSA (Prostate Specific Antigene) nor the epithelial-cell-specific marker CK20 (Cytokeratin 20) can be, detected in the corresponding tumor cells. Actin is used as RT-PCR positive control.

Figure 10:
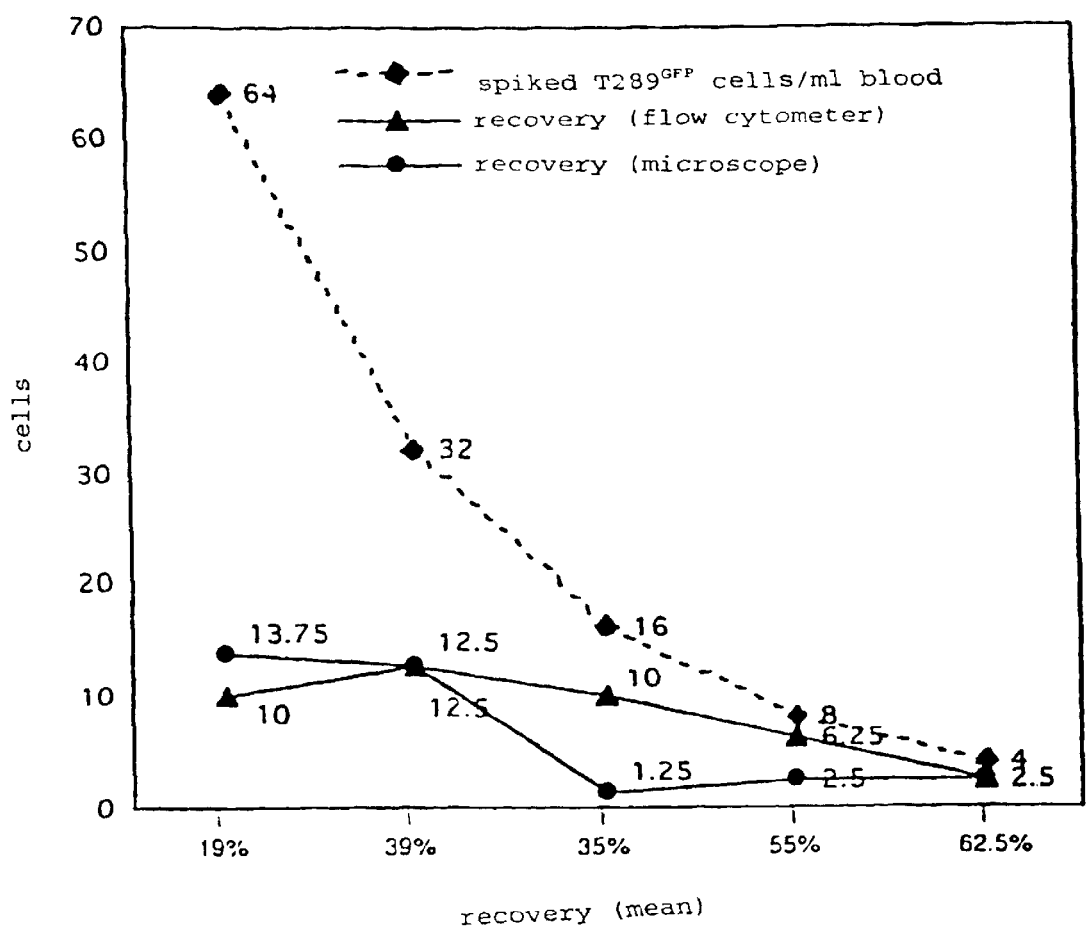
FIG. 10 shows the recovery rate of GFP-transfected melanoma cells which were mixed into blood of different (A, B) healthy donors, after a concentration using a cell separation medium of a density of 1.065 g/ml.
Figure 10:
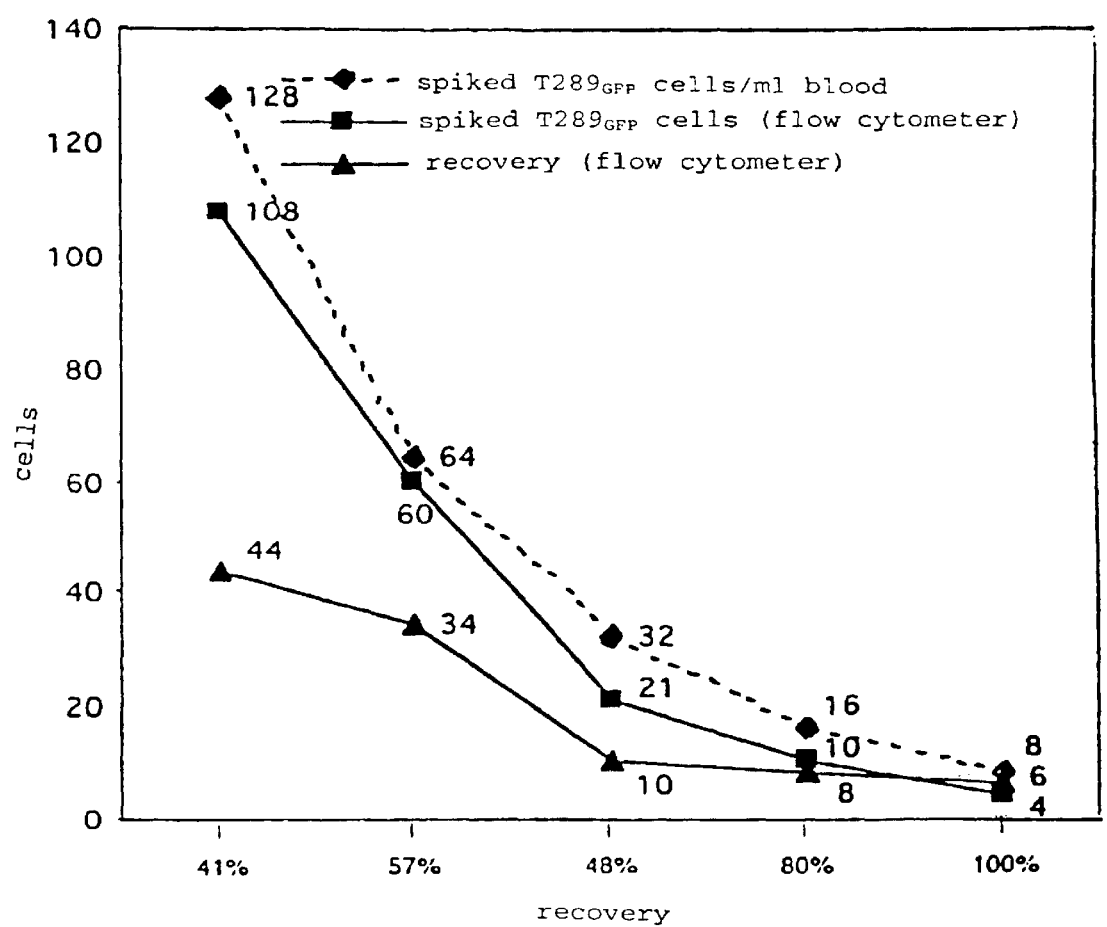

FIG. 10 shows the recovery rates of GFP-transfected melanoma cells (T289) which had been admixed with blood samples of healthy donors (spiked). The spiked blood samples were then applied as a layer onto Percoll of a density of 1.065 g/ml and centrifuged, and the number of reisolated tumor cells (recovery) was determined microscopically (-●-) and/or by flow cytometry (-▲-). Since only about 75% and 50% of the GFP-transfected T289 cells could be detected in the flow cytometer for sample A and sample B, respectively, the recovery rates were corrected correspondingly. The recovery rate of spiked tumor cells depends on the blood donor in question (the blood samples of A) and B) originate from different donors) and the cell line used and is inversely proportional to the number of spiked tumor cells. It is possible for a rejection reaction of the corresponding hematopoietic cells to lead to lysis, aggregation and finally loss of the spiked allogenic tumor cells. In addition, B) shows that the number of the actual spiked tumor cells (-■-) is 6%–37% lower than the theoretical number of spiked tumor cells (-♦-).

Taking into account investigations with lung and mamma carcinoma cells, not shown here, an average recovery rate with the concentration method preferred according to the invention is 46%±20% for 4–512 spiked cells (n=16) and 54%±20% (n=15) for ≦50 spiked cells.

The recovery rate of the tumor cell concentration method which is preferred according to the invention is thus approximately in the range of magnetic cell separators such as MACS, for which the stated recovery rate is about 30–58%.

2. Cultivation and Isolation of Peripheral Blood, Tissue and Cells for the Examples Below Tumor cell lines such as the human prostate carcinoma cell line LNcap and the teratocarcinoma cell line Tera 2 were cultured as recommended by the ATCC (American Tissue Culture Collection). Venous blood donated by healthy control subjects was taken by puncture of a forearm vein in EDTA monovets® (Saarsted).

3. Isolation of Cellular RNA

Figure 7:
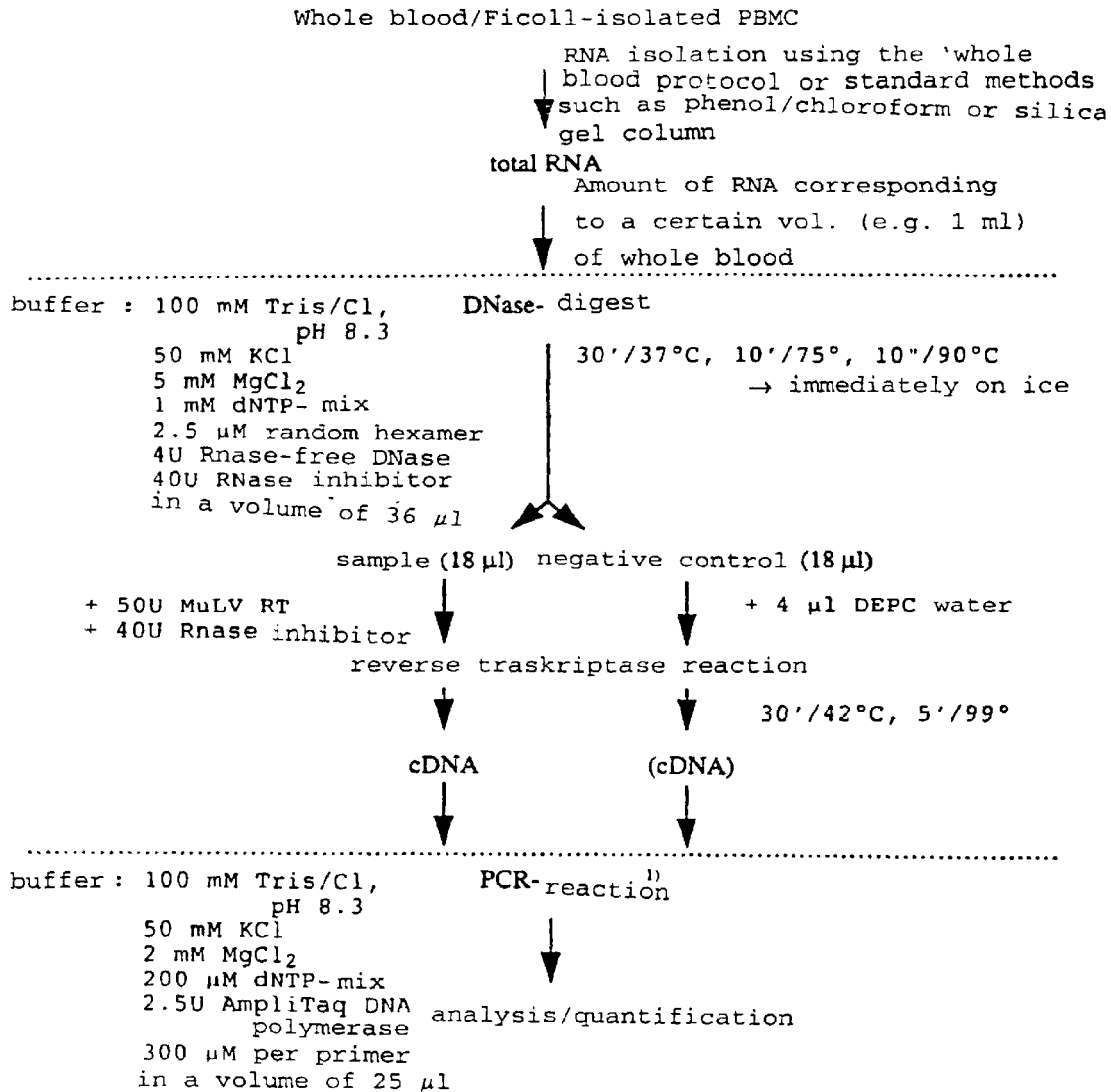
As shown in FIG. 7, the PCR was carried out using specific primers (FIG. 6) for the catalytic subunit of human telomerase (A) and β-actin, for 40 cycles. Under the RT-PCR conditions described, the mRNA coding for the catalytic subunit of human telomerase can be demonstrated in up to 10 cells (arrow). To exclude DNA contaminations, RNA from $10^3$ cells without reverse transcriptase as control reaction and a water control ($H_2O$) were also tested in the RT-PCR.

Total cellular RNA was isolated by standard methods [Chomczynski et al. (1987) Anal Biochem 162, 156; Sambrook, J. et al. (1989). Cold Spring Harbor, N.Y., USA, Cold Spring Harbor Laboratory Press]. Peripheral blood was transferred and homogenized, as shown in FIG. 7, immediately after removal into RNA lysis buffer (4 M guanidinium isothiocyanate; 0.1 M Tris-HCl, pH 7.5; 1% mercaptoethanol). The mixtures were either immediately processed further or stored at −70° C.

4. Reverse Transcription and Polymerase Chain Reaction (RT-PCR)

The RT-PCR was carried out, as shown in FIG. 7, with the GeneAmp® RNA-PCR kit (Perkin Elmer) as specified by the manufacturer. Aliquots of the isolated total RNA from peripheral blood and cell lines were in each case previously hydrolyzed with 4 U of DNase and 40 U of RNAse inhibitor (Boehringer, Mannheim) in 36 µl mixtures (in 100 mM Tris-HCl, pH 8.3; 50 mM KCl; 5 mM $MgCl_2$, 1 mM dNTP mix and 2.5 mM random hexamers) at 37° C. for 30 minutes and then at 75° C. for 10 minutes and then the DNAse was inactivated at 90° C. for 10 minutes and the reaction mixture was immediately stored in ice.

The two oligonucleotide primers:

5' CTACCGGAAG AGTGTCTGGA GCAAGTTGCA AAGC 3' (hTRT1) (SEQ. ID. NO. 1) and

5' GGCATACCGA CGCACGCAGT ACGTGTTCTG 3' (hTRT2) (SEQ ID. NO. 2)

were designed in accordance with the sequence, published by Nakamura et al., coding for the catalytic subunit of human telomerase (Nakiamura et al. (1997). Science 277: 955–9) (FIG. 1 and SEQ ID. NO. 10) and synthesized using an Applied Biosystem 380A synthesizer. The specificity of the hTRT1 and hTRT2 primers was checked by computer-assisted analysis of homology on the nucleic acid sequences in the GenBank, EMBL, DDBJ and PDB databases using BLASTIN 1.4.9 MP (Altschul, S. F. et al. (1990), J Mol Biol 215: 403–410].

For consistency of the amplified amounts, the same amounts of RNA were employed for the RT reaction in each experiment. In order to preclude contamination of the RNA preparations with genomic DNA, each RNA-containing sample hydrolyzed with DNAse was first subjected to the PCR described below and checked for amplification. The RNA-containing sample in which no amplification product was detectable was employed for the subsequent cDNA synthesis and PCR steps. Oligonucleotide primers for β-actin and TCR were employed as internal standard control (FIG. 6). The reverse transcriptase reaction was carried out using 18 μl of the DNAse digest, with addition of 50 U MuLV reverse transcriptase and 40 U RNAse inhibitor, at 42° C. for 30 minutes, and the reaction was terminated at 99° C. for 5 minutes. In the negative controls, 40 μl of water were added instead of the enzymes.

The PCR was carried out, as shown in FIG. 7, on 5 μl of the cDNA reaction using the following program: (97° C.: 15 seconds, preheating); (97° C: 15 seconds, 70° C.: 30 seconds [minus 0.5° C. per cycle], 72° C.: 30 seconds) 10 cycles; (94° C.: 15 seconds, 65° C.: 30 seconds [minus 0.5° C. per cycle], 72° C.: 30 seconds) 20 cycles; (94° C.: 15 seconds, 50° C.: 30 seconds, 72° C.: 30 seconds [plus 15 seconds extension per cycle], 10 cycles; (72° C.: 7 minutes, final extension).

The amplification products were fractionated by gel electrophoresis on 1.5% TAE agarose gel, stained with ethidium bromide and visualized and recorded by photography under UV light (see FIGS. 2–5).

5. Preparation of Possible Standard RNA Nucleic Acids (hTRTKa, hTRTKb and hTRTKc)

The PCR amplification products intended for cloning can be fractionated by gel electrophoresis on 1.5% TAE agarose and eluted (Qiagen). The restriction hydrolysates can be purified by phenol/chloroform extraction and precipitated in salt and ethanol or by DNA purification (Qiagen). The constructs can be created, for example, by ligating the fragments into the corresponding cleavage sites in a cloning and transcription vector, for example pGEM-13Zf(+), using T4 ligase. This vector permits in vitro transcription of cloned fragments by use of Sp6 or T7 RNA polymerases as selected. Competent bacteria (XL-1Blue, Stratagene) are transformed by electroporation (BioRad). Plasmid DNA is purified using plasmid purification kits (Qiagen). Positive clones are validated using vector- or sequence-specific oligonucleotide primers with the PCR. Sequence validation can be carried out for the constructs by semiautomatic sequence analysis.

The construct pGEM-hTRT is created as initial construct for the constructs pGEM-hTRT(Ka), pGEM-hTRT(Kb) and pGEM-hTRT(Kc). pGEM-hTRT(Ka) pGEM-hTRT(Kb) and pGEM-hTRT(Kc) differ from pGEM-hTRT and from one another by a randomized exchange of sequence of about 20 base pairs (bp). The constructs are used for in vitro transcription with Sp6 RNA polymerase of the standard RNA: hTRT(Ka), hTRT(Kb) and hTRT(Kc). To form the construct pGEM-hTRT, the cDNA of the catalytic subunit of human telomerase (FIG. 1 and SEQ ID. NO. 10) is cloned, for example, into the NotI and HindIII cleavage sites of pGEM-13Zf(+). This is achieved by carrying out an RT-PCR with these cleavage-site-containing oligonucleotide primers, which are derived from the sequence hTRT (FIG. 1 and SEQ ID. NO. 10), on the previously isolated RNA from tumor cells or lines under the conditions described above. Thus, it is possible, for example, to amplify the full-length hTRT with given cleavage sites, or a shorter fragment. After a restriction hydrolysis with specific restriction enzymes, for example NotI and HindIII, the fragment formed is cloned into the corresponding cleavage sites (for example position 12 or 38) of pGEM-13Zf(+) and the construct pGEM-hTRT is created. pGEM-hTRT(Ka) is constructed by replacing an about 20 bp sequence in the construct pGEM-hTRT is created. pGEM-hTRT(Ka) is constructed by replacing an about 20 bp sequence in the construct pGEM-hTRT by an about 20 bp cassette. This replacement is carried out by recombinant PCR and is a modification of the method described by Higuchi et al. [Higuchi, R. (1988). Nucleic Acid Res 16: 7351–7367; Higuchi, R. (1990). M. Innis A. et al. Eds. San Diego, New York, Berkley, Boston, London, Sydney, Tokyo, Toronto, Academic Press, Inc. 177–183]. In a first step, two independent PCR reactions are carried out on pGEM-hTRT: the amplification product from the 1st PCR gives the 5' fragment and is digested with suitable restriction enzymes to give a 5' fragment. The amplification product from the 2nd PCR reaction gives the 3' fragment and is hydrolyzed with suitable restriction enzymes to give a 3' fragment. Using T4 ligase, the cleavage sites of the 5' and 3' fragments are connected to give a fragment which is cloned into the corresponding cleavage sites of pGEM-13Zf(+), to create the construct pGEM-hTRT(Ka). pGEM-hTRT(Kb) and pGEM-hTRT(Kc) are constructed by replacing the about 20 bp sequence, created above, in the construct pGEM-hTRT(Ka), in each case with a randomized sequence of about 20 bp. RNA can then be produced in vitro from pGEM-hTRT(Ka), pGEM-hTRT(Kb) and pGEM-hTRT(Kc) with Sp6 RNA polymerase. The specific RNAs can then be detected with oligonucleotides O(Ka), O(Kb), O(Kc) and W(wt), which are complementary to the abovementioned about 20 bp replacement sequences and to the wild-type sequence (wt), respectively. The further processing of the RNA, such as DNAse digestion, purification and calibration, is carried out by standard methods.

6. Results

Figure 3:
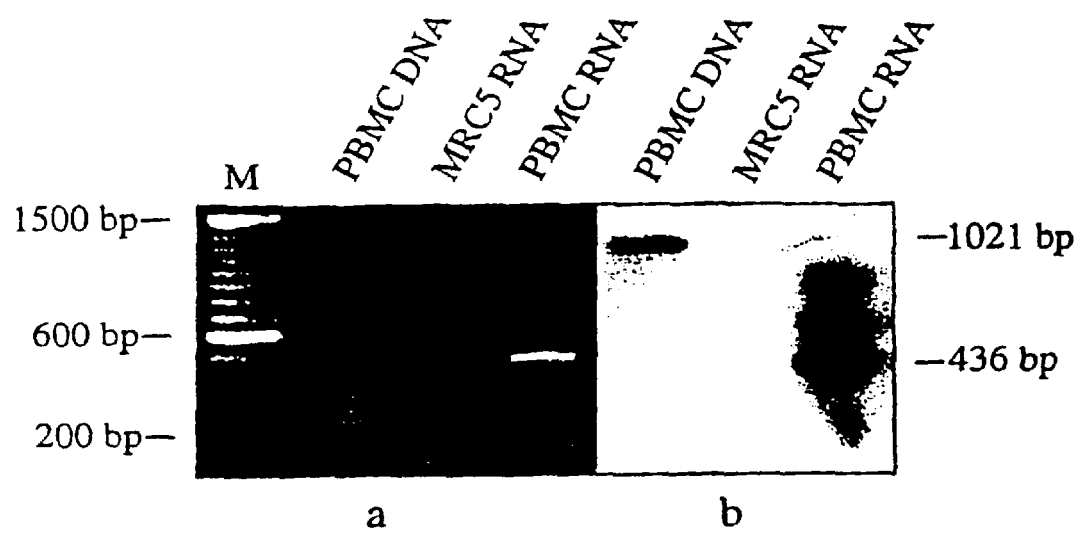
FIG. 3 shows an agarose gel electrophoresis (a) of the RT-PCR products with TCT-specific primers on RNA and DNA of human PBMC and the human fibroblast cell line MRC5 and the corresponding Southern blot analysis with a TCR-specific oligonucleotide probe (TCT probe). M: marker.
Figure 4:
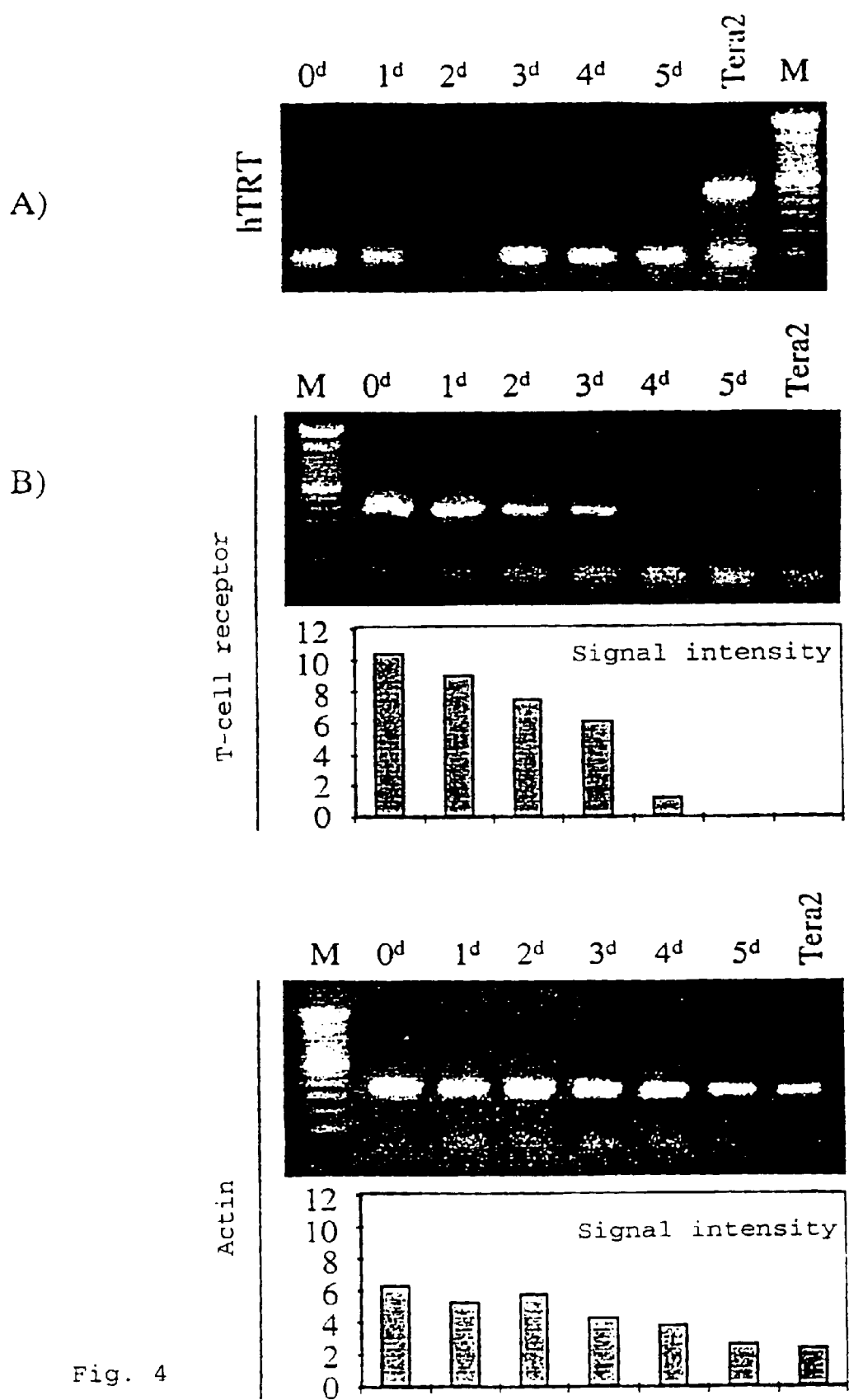
FIG. 4 shows an agarose gel electrophoresis of the RT-PCR products with specific primers for hTRT (A) and TCR and actin (B) on RNA which had been isolated from 1 ml of whole blood, after cultivation for 0–5 days, and a reaction on the RNA of the human teratocarcinoma cell line Tera2. Bands $0^d$–$5^d$: culture period of 0 to 5 days, respectively. M: marker, Tera2: human teratocarcinoma cell line Tera2.
Figure 5:
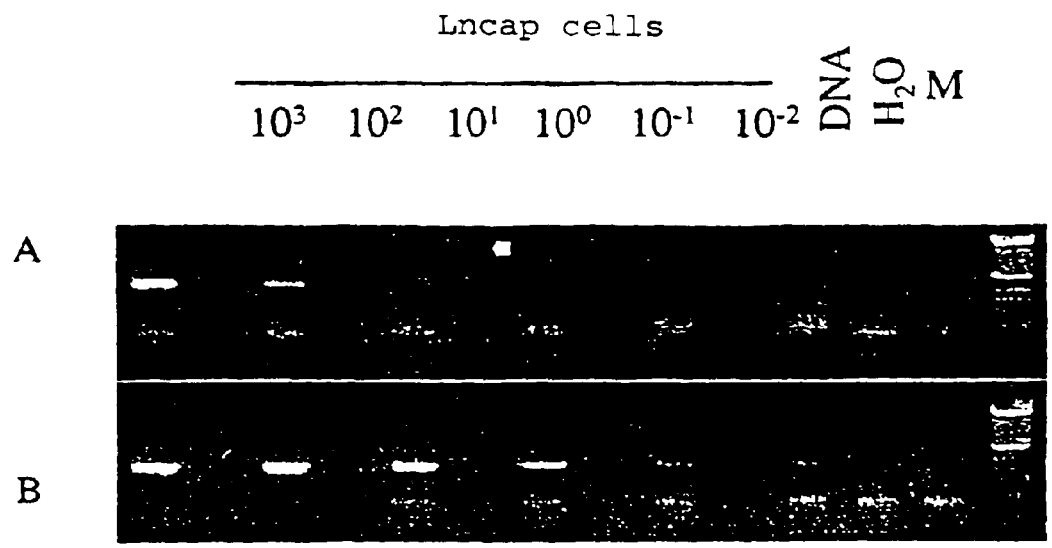
FIG. 5 shows an agarose gel electrophoresis of the RT-PCR products on RNA of the prostate carcinoma cell line LNcap. Bands $10^3$–$10^{-2}$: number of cells used per experiment. DNA: DNA control. $H_2O$: water control. M: marker.

The investigations on tumor cell lines revealed that the mRNA which codes for the catalytic subunit of human telomerase was detectable in different amounts in tumor cell lines with the same amount amplified in the TCR or β-actin control reaction (FIGS. 2, 4 and 5). It was possible to rule out contamination with genomic DNA in each case by a control reaction without addition of reverse transcriptase.

In comparative investigations, using whole-blood cultivations of different durations, it was shown unambiguously that, after cultivation of the whole blood for 1–5 days, no more specific RT-PCR product of the catalytic subunit of human telomerase could be detected. In parallel, with increasing duration of the culture, the amount of specific TCR- and actin-RNA decreased much more slowly. The result of these cultivation investigations is that evidently contaminating telomerase-positive nontumor cells have died as early as between day 0 and day 1.

Furthermore, under the RT-PCR conditions described with differing amounts of telomerase-positive tumor cells, the catalytic subunit of human telomerase can be detected in up to 10 cells.

Since, in contrast to the TRAP assay, highly purified RNA is used for amplification in the reverse transcriptase polymerase chain reaction (RT-PCR) method used according to the invention, an inhibition of Taq polymerase can be substantially excluded. In addition, for the RT-PCR method described, a sensitivity for the detection of the RNA component (hTR) and the catalytic subunit (hTRT) of telomerase of about 1 cell per RT-PCR mixture was demonstrated. Thus, the use of the RT-PCR method described offers a comparable or better sensitivity for the detection of telomerase-active tumor cells. Additionally, it was shown that the detection of hTR and hTRT expression correlates with the catalytic activity of telomerase (K. Yashima et al., J. Clin. Pathol. (1997), 50, 110–7).

What is claimed is:

1. A method for the quantification of tumor cells in a body fluid, comprising:
   (a) concentrating tumor cells in a sample of a body fluid by covering a cell separation medium with a density in the range of from 1.060–1.065 g/ml with a layer of the body fluid, centrifuging the cell separation medium covered with the body fluid and collecting the tumor cells at the interface of the cell separation medium and the supernatant body fluid;
   (b) specifically amplifying, from the tumor cells, mRNA coding for the catalytic subunit of telomerase;
   (c) quantitatively determining the amount of amplified nucleic acid; and
   (d) correlating the amount of amplified nucleic acid with the number of tumor cells in the body fluid.

2. The method of claim 1, further comprising prior to amplification, preparing cDNA from the mRNA contained in the sample.

3. The method of claim 2, wherein, prior to preparing cDNA, the sample is treated with a DNAase.

4. The method of claim 1, wherein the sample is gel purified.

5. The method of claim 1, wherein for quantitative determination of the telomerase-coding nucleic acid, the amplification products are labeled during amplification and the amplification kinetics are measured continuously, including during the amplification process.

6. The method of claim 5, wherein a probe that is specific for the amplification products, and that emits a characteristic signal proportional to the products amplified per synthesis cycle, is present during amplification.

7. The method of claim 1, wherein for quantitative determination of the telomerase-encoding nucleic acid, at least one standard nucleic acid molecule is coamplified and added in different concentrations to the sample.

8. The method of claim 1, wherein the amplification product is quantified either directly or via a label.

9. The method of claim 1, wherein the amplification product is detected via hybridization with a labeled oligonucleotide.

10. The method of claim 7, wherein quantification of the telomerase-encoding nucleic acid is effected by comparing the amount of coamplified nucleic acid or nucleic acids with the amount of telomerase-encoding nucleic acid.

11. The method of claim 1, wherein the sample is peripheral blood.

12. The method of claim 1, wherein as a negative control water is employed in place of the body fluid.

13. The method of claim 1, wherein one or both of the following oligonucleotide primers are used for the amplification:
   5' CTACCGGAAG AGTGTCTGGA GCAAGTTGGA AAGC 3' SEQ ID No. 1, designated TRT1; and
   5' GGCATACCGA CGCACGCAGT ACGTGTTCTG 3' SEQ ID No.2, designated TRT2,
   wherein each of hTRT1 and hTRT2 optionally further comprises a promoter sequence for an RNA polymerase.

14. The method of claim 1, wherein amplification is effected with a DNA polymerase or an RNA polymerase.

15. The method of claim 14, wherein, if amplification is effected with a DNA polymerase, the amplification reaction is a polymerase chain reaction (PCR) and, if amplification is effected with an RNA polymerase, the reaction is an isothermal nucleic acid sequence-based amplification (NASBA) reaction.

16. The method of claim 1, wherein the sample is blood that is depleted in stem cells and/or activated immune cells.

17. The method of claim 1, wherein the sample is blood, and the tumor cells from the blood sample are concentrated.

18. The method of claim 1, wherein the cells contained in the sample are cultivated under conditions that are unfavorable for telomerase-positive nontumor cells but favorable for the tumor cells present.

19. The method of claim 18, wherein the duration of the cultivation is such that nontumor cells die and tumor cells survive.

20. The method of claim 1, wherein the centrifugation is carried out at about 1000×g for about 30 minutes.

21. The method of claim 1, wherein the cell separation medium used is Percoll or Ficoll.

22. The method of claim 1, wherein the body fluid is blood and prior to applying the body fluid sample to the cell separation medium, the body fluid is mixed with one or more substances that prevent aggregation of platelets to tumor cells, and/or prior to applying the body fluid sample to the cell separation medium, the body fluid is freed of substances that promote aggregation of platelets to tumor cells.

23. The method of claim 11, wherein the peripheral blood is drawn in an anticoagulant substance and, prior to covering the cell separation medium, diluted with a diluent.

24. The method of claim 11, wherein the peripheral blood is venous or arterial blood.

25. The method of claim 1, wherein the body fluid is selected from the group consisting of lymph, urine, exudates, transudates, spinal fluid, seminal fluid, saliva, fluids from natural or unnatural body cavities, bone marrow and dispersed body tissue.

26. The method of claim 1, wherein after centrifugation and before collecting the tumor-cell-enriched interface, the centrifugation vessel is removed and cooled to prevent mixing of the cells in the different layers.

27. The method of claim 1, wherein the centrifugation is carried out in a vessel that is divided by a porous barrier, a filter or a sieve into an upper and a lower compartment and the body fluid is introduced into the upper compartment.

28. The method of claim 27, wherein at least one of the porous barrier, the filter or the sieve has a thickness of 1–10 mm.

29. The method of claim 27, wherein at least one of the porous barrier, the filter or the sieve has a pore size of 20–100 $\mu$m.

30. The method of claim 27, wherein at least one of the porous barrier, the filter or the sieve is fabricated from a hydrophobic material or coated with a hydrophobic material.

31. The method of claim 1, wherein a dye is added to color the cell separation medium, whereby the color of the cell separation medium is distinguishable from that of the supernatant body fluid.

32. The method of claim 1, wherein: the sample is blood;
the method is performed on venous blood sample and on an arterial blood sample; and the results from each are compared with one another.

33. The method of claim 1, wherein: the sample is blood;
the method is performed on a blood sample from the finger pad and, on a venous or arterial blood sample; and
the results from each are compared with one another.

34. The method of claim 1, wherein the tumor cells are derived from metastases of malignant tumors.

35. The method of claim 1, wherein the tumor cells are selected from cells of metastasizing tumors and/or neoplasms, wherein the cells are derived from tumors and cells selected from the group consisting of a T-cell lymphoblastoma, T-cell leukemia cells, chronic myeloid leukemia cells, acute lymphatic leukemia cells, chronic lymphatic leukemia cells, teratocarcinoma, melanoma, carcinoma of the lung, large intestine cancer, breast cancer, hepatocellular carcinoma, kidney tumor, adrenal tumor, prostate carcinoma, neuroblastoma, brain tumor, rhabdomyosarcoma, leiomyosarcoma and lymphoma cells.

36. The method of claim 4, wherein purification is effected by ion exchange chromatography.

37. The method of claim 36, wherein ion exchange resin is a silica gel.

38. The method of claim 7, wherein three standard nucleic acids are coamplified and are added in different concentrations to the sample.

39. The method of claim 8, wherein:
the amplification product is quantified via a label; and
the label is selected from a radioactive label, a biotin label, a fluorescent label or an electrochemoluminescent label.

40. The method of claim 9, wherein the label is a radioactive label, a biotin label, a fluorescent label or an electrochemoluminescent label.

41. The method of claim 11, wherein, as a positive control in the sample, a nucleic acid that occurs in peripheral blood is specifically amplified and detected.

42. The method of claim 41, wherein the nucleic acid is mRNA that encodes a protein selected from among $\beta$-globin, glyceraldehyde-phosphate dehydrogenase, $\beta$-actin or a T-cell receptor.

43. The method of claim 3, wherein as a negative control no reverse transcription reaction is carried out before the amplification reaction with the sample to be investigated and/or water is employed in place of the body fluid.

44. The method of claim 16, wherein depletion is effected by immunoabsorption.

45. The method of claim 17, wherein concentration is effected by immunoabsorption.

46. The method of claim 1, wherein the density is about 1.065 g/ml.

47. The method of claim 11, wherein the peripheral blood is drawn in an anticoagulant substance and, prior to covering the cell separation medium, diluted with a diluent at a ratio of about 1:1.

48. The method of claim 28, wherein at least one of the porous barrier, the filter or the sieve has a thickness of about 5 mm.

49. The method of claim 27, wherein at least one of the porous barrier, the filter or the sieve has a pore size of 20–30 $\mu$m.

50. The method of claim 1, wherein the tumor cells are derived from micrometastases of malignant tumors.

* * * * *

SEQUENCE LISTING

<160> NUMBER OF SEQ ID NOS: 10

<210> SEQ ID NO 1
<211> LENGTH: 34
<212> TYPE: DNA
<213> ORGANISM: Homo sapiens
<220> FEATURE:
<223> OTHER INFORMATION:

<400> SEQUENCE: 1
ctaccggaag agtgtctgga gcaagttgca aagc                          34

<210> SEQ ID NO 2
<211> LENGTH: 30
<212> TYPE: DNA
<213> ORGANISM: Homo sapiens
<220> FEATURE:
<223> OTHER INFORMATION:

<400> SEQUENCE: 2
ggcataccga cgcacgcagt acgtgttctg                                30

<210> SEQ ID NO 3
<211> LENGTH: 20
<212> TYPE: DNA
<213> ORGANISM: Homo sapiens
<220> FEATURE:
<223> OTHER INFORMATION:

<400> SEQUENCE: 3
acccagaggt tctttgagtc                                           20

<210> SEQ ID NO 4
<211> LENGTH: 20
<212> TYPE: DNA
<213> ORGANISM: Homo sapiens
<220> FEATURE:
<223> OTHER INFORMATION:

<400> SEQUENCE: 4
tctgataggc agcctgcact                                           20

<210> SEQ ID NO 5
<211> LENGTH: 24
<212> TYPE: DNA
<213> ORGANISM: Homo sapiens
<220> FEATURE:
<223> OTHER INFORMATION:

<400> SEQUENCE: 5
gatgatgata tcgccgcgct cgtc                                      24

<210> SEQ ID NO 6
<211> LENGTH: 25
<212> TYPE: DNA
<213> ORGANISM: Homo sapiens
<220> FEATURE:
<223> OTHER INFORMATION:

<400> SEQUENCE: 6
ctcaaacatg atctgggtca tcttc                                     25

<210> SEQ ID NO 7
<211> LENGTH: 28

```
<212> TYPE: DNA
<213> ORGANISM: Homo sapiens
<220> FEATURE:
<223> OTHER INFORMATION:

<400> SEQUENCE: 7
gaggtcgctg tgtttgagcc atcagaag                                          28

<210> SEQ ID NO 8
<211> LENGTH: 27
<212> TYPE: DNA
<213> ORGANISM: Homo sapiens
<220> FEATURE:
<223> OTHER INFORMATION:

<400> SEQUENCE: 8
gatctcatag aggatggtgg cagacag                                           27

<210> SEQ ID NO 9
<211> LENGTH: 24
<212> TYPE: DNA
<213> ORGANISM: Homo sapiens
<220> FEATURE:
<223> OTHER INFORMATION:

<400> SEQUENCE: 9
cgttctggct cccacgacgt agtc                                              24

<210> SEQ ID NO 10
<211> LENGTH: 4015
<212> TYPE: DNA
<213> ORGANISM: Homo sapiens
<220> FEATURE:
<223> OTHER INFORMATION:

<400> SEQUENCE: 10
gcagcgctgc gtcctgctgc gcacgtggga agccctggcc ccggccaccc ccgcgatgcc        60
gcgcgctccc cgctgccgag ccgtgcgctc cctgctgcgc agccactacc gcgaggtgct       120
gccgctggcc acgttcgtgc ggcgcctggg gccccagggg tggcggctgg tgcagcgcgg       180
ggacccggcg gctttccgcg cgctggtggc ccagtgcctg gtgtgcgtgc cctgggacgc       240
acggccgccc ccgccgcc cctccttccg ccaggtgtcc tgcctgaagg agctggtggc        300
ccgagtgctg cagaggctgt gcgagcgcgg cgcgaagaac gtgctggcct tcggcttcgc       360
gctgctggac ggggcccgcg ggggcccccc cgaggccttc accaccagcg tgcgcagcta       420
cctgcccaac acggtgaccg acgcactgcg ggggagcggg gcgtgggggc tgctgctgcg       480
ccgcgtgggc gacgacgtgc tggttcacct gctggcacgc tgcgcgctct ttgtgctggt       540
ggctcccagc tgcgcctacc aggtgtgcgg gccgccgctg taccagctcg gcgctgccac       600
tcaggcccgg cccccgccac acgctagtgg acccgaagg cgtctgggat gcgaacgggc        660
ctggaaccat agcgtcaggg aggccggggt cccccctggg ctgccagccc cgggtgcgag       720
gaggcgcggg ggcagtgcca gccgaagtct gccgttgccc aagaggccca ggcgtggcgc       780
tgcccctgag ccggagcgga cgcccgttgg gcagggggtcc tgggcccacc cgggcaggac       840
gcgtggaccg agtgaccgtg gtttctgtgt ggtgtcacct gccagacccg ccgaagaagc       900
cacctctttg gagggtgcgc tctctggcac gcgccactcc cacccatccg tgggccgcca       960
gcaccacgcg ggccccccat ccacatcgcg gccaccacgt ccctgggaca cgccttgtcc      1020
cccggtgtac gccgagacca agcacttcct ctactcctca ggcgacaagg agcagctgcg      1080
```

-continued

```
gccctccttc ctactcagct ctctgaggcc cagcctgact ggcgctcgga ggctcgtgga    1140
gaccatcttt ctgggttcca ggccctggat gccaggact ccccgcaggt tgccccgcct    1200
gccccagcgc tactggcaaa tgcggcccct gtttctggag ctgcttggga accacgcgca    1260
gtgcccctac ggggtgctcc tcaagacgca ctgcccgctg cgagctgcgg tcaccccagc    1320
agccggtgtc tgtgcccggg agaagcccca gggctctgtg gcggccccg aggaggagga    1380 cacagacccc cgtcgcctgg tgcagctgct ccgccagcac agcagcccct ggcaggtgta    1440
cggcttcgtg cgggcctgcc tgcgccggct ggtgccccca ggcctctggg ctccaggca    1500 caacgaacgc cgcttcctca ggaacaccaa gaagttcatc tccctgggga agcatgccaa    1560
gctctcgctg caggagctga cgtggaagat gagcgtgcgg gactgcgctt ggctgcgcag    1620
gagcccaggg gttggctgtg ttccggccgc agagcaccgt ctgcgtgagg agatcctggc    1680
caagttcctg cactggctga tgagtgtgta cgtcgtcgag ctgctcaggt ctttctttta    1740
tgtcacggag accacgtttc aaaagaacag gctctttttc taccggaaga gtgtctggag    1800
caagttgcaa agcattggaa tcagacagca cttgaagagg gtgcagctgc gggagctgtc    1860
ggaagcagag gtcaggcagc atcgggaagc caggcccgcc ctgctgacgt ccagactccg    1920
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggtgga tgtgacgggc gcgtacgaca ccatccccca    2220
ggacaggctc acggaggtca tcgccagcat catcaaaccc cagaacacgt actgcgtgcg    2280
tcggtatgcc gtggtccaga aggccgccca tgggcacgtc cgcaaggcct tcaagagcca    2340
cgtctctacc ttgacagacc tccagccgta catgcgacag ttcgtggctc acctgcagga    2400
gaccagcccg ctgagggatg ccgtcgtcat cgagcagagc tcctccctga atgaggccag    2460
cagtggcctc ttcgacgtct tcctacgctt catgtgccac cacgccgtgc gcatcagggg    2520
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct cacctcaccc acgcgaaaac    2700
cttcctcagg accctggtcc gaggtgtccc tgagtatggc tgcgtggtga acttgcggaa    2760
gacagtggtg aacttccctg tagaagacga ggccctgggg ggcacggctt ttgttcagat    2820
gccggcccac ggcctattcc cctggtgcgg cctgctgctg gatacccgga ccctggaggt    2880
gcagagcgac tactccagct atgcccgac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccatttca    3120
tcagcaagtt tggaagaacc ccacattttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctggggtca ctcaggacag cccagacgca    3360
gctgagtcgg aagctcccgg ggacgacgct gactgccctg gaggccgcag ccaacccggc    3420
actgccctca gacttcaaga ccatcctgga ctgatggcca cccgcccaca gccaggccga    3480
```

```
gagcagacac cagcagccct gtcacgccgg gctctacgtc ccagggaggg aggggcggcc    3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc cccaccatcc    3840
aggtggagac cctgagaagg accctgggag ctctgggaat ttggagtgac caaaggtgtg    3900
ccctgtacac aggcgaggac cctgcacctg gatgggggtc cctgtgggtc aaattggggg    3960
gaggtgctgt gggagtaaaa tactgaatat atgagttttt cagttttgaa aaaaa        4015
```